United States Patent
Kono et al.

(10) Patent No.: US 11,008,408 B2
(45) Date of Patent: May 18, 2021

(54) ALKOXYMAGNESIUM, METHOD FOR PRODUCING ALKOXYMAGNESIUM, SOLID CATALYST COMPONENT FOR OLEFIN POLYMERIZATION, OLEFIN POLYMERIZATION CATALYST, AND METHOD FOR PRODUCING OLEFIN POLYMER

(71) Applicant: TOHO TITANIUM CO., LTD., Chigasaki (JP)

(72) Inventors: Hiroyuki Kono, Chigasaki (JP); Shingo Yamada, Chigasaki (JP); Toshiya Uozumi, Chigasaki (JP)

(73) Assignee: TOHO TITANIUM CO., LTD., Kanagawa (JP)

( * ) Notice: Subject to any disclaimer, the term of this patent is extended or adjusted under 35 U.S.C. 154(b) by 257 days.

(21) Appl. No.: 16/088,158

(22) PCT Filed: Mar. 23, 2017

(86) PCT No.: PCT/JP2017/011589
§ 371 (c)(1),
(2) Date: Sep. 25, 2018

(87) PCT Pub. No.: WO2017/170077
PCT Pub. Date: Oct. 5, 2017

(65) Prior Publication Data
US 2020/0299422 A1    Sep. 24, 2020

(30) Foreign Application Priority Data
Mar. 28, 2016  (JP) .............. JP2016-063506

(51) Int. Cl.
*C07C 29/70* (2006.01)
*C07C 31/30* (2006.01)
*C08F 4/52* (2006.01)
*C08F 10/06* (2006.01)
*C07F 3/02* (2006.01)
*C08F 4/642* (2006.01)

(52) U.S. Cl.
CPC .............. *C08F 10/06* (2013.01); *C07C 29/70* (2013.01); *C07F 3/02* (2013.01); *C07C 31/30* (2013.01); *C08F 4/6425* (2013.01)

(58) Field of Classification Search
CPC .... C08F 4/6421; C08F 4/6425; C08F 4/6426; C07C 29/70; C07C 31/30
See application file for complete search history.

(56) References Cited

U.S. PATENT DOCUMENTS

| | | | | |
|---|---|---|---|---|
| 4,330,649 A * | 5/1982 | Kioka | ............... | C08F 4/022 526/124.9 |
| 4,399,055 A * | 8/1983 | Matsuura | ............... | C08F 10/00 502/104 |
| 4,654,318 A * | 3/1987 | Yamamoto | ............... | C08F 10/00 502/119 |
| 5,629,390 A * | 5/1997 | Nishimura | ............... | C08F 10/00 526/114 |
| 5,965,478 A * | 10/1999 | Goto | ............... | C08F 10/00 502/127 |
| 6,287,705 B1 * | 9/2001 | Seta | ............... | B32B 27/32 428/500 |
| 8,426,537 B2 * | 4/2013 | Hosaka | ............... | C08F 10/06 526/116 |
| 8,632,882 B2 * | 1/2014 | Yamanaka | ............... | C07C 29/70 428/402 |
| 8,957,166 B2 * | 2/2015 | Kobayashi | ............... | B01J 8/228 526/65 |
| 9,493,586 B2 * | 11/2016 | Kobayashi | ............... | C08F 4/06 |
| 2002/0045537 A1 * | 4/2002 | Yang | ............... | C08F 110/02 502/158 |
| 2008/0281059 A1 * | 11/2008 | Tanase | ............... | C07C 31/28 526/123.1 |
| 2009/0202833 A1 | 8/2009 | Yamanaka et al. | | |
| 2009/0233793 A1 * | 9/2009 | Park | ............... | C07C 29/70 502/439 |
| 2017/0355792 A1 * | 12/2017 | Wang | ............... | C07C 29/70 |

FOREIGN PATENT DOCUMENTS

| | | |
|---|---|---|
| CN | 101415666 B | 7/2013 |
| EP | 2006272 A1 | 12/2008 |
| JP | 2000-143731 A | 5/2000 |
| JP | 2004-268909 A | 9/2004 |
| JP | 2004-269467 A | 9/2004 |
| JP | 2005-75995 A | 3/2005 |
| JP | 2005-120123 A | 5/2005 |

(Continued)

OTHER PUBLICATIONS

International Search Report dated May 30, 2017, issued in counterpart International Application No. PCT/JP2017/011589 (2 pages).

(Continued)

*Primary Examiner* — Rip A Lee
(74) *Attorney, Agent, or Firm* — Westerman, Hattori, Daniels & Adrian, LLP

(57) ABSTRACT

There is provided a novel alkoxymagnesium which, when used as a constituent of a solid catalyst component for olefin polymerization to polymerize an olefin, may reduce the formation rate of a fine powder and may form a polymer having an excellent particle size distribution under high polymerization activity. The alkoxymagnesium is characterized by comprising secondary particles each of which is an aggregate of primary particles having an average particle diameter of less than 1 μm and by having a ratio represented by the average particle diameter of the primary particles/the average particle diameter of the secondary particles of 0.1 or less, a total pore volume of 0.5 to 1 $cm^3/g$, a specific surface area of less than 50 $m^2/g$, and a particle size distribution index (SPAN) 1 or less.

15 Claims, 2 Drawing Sheets

(56) References Cited

FOREIGN PATENT DOCUMENTS

| | | |
|---|---|---|
| JP | 2007-297371 A | 11/2007 |
| JP | 2008-285573 A | 11/2008 |
| JP | 2010-30925 A | 2/2010 |
| JP | 2013-95890 A | 5/2013 |

OTHER PUBLICATIONS

Office Action dated Aug. 10, 2020, issued in counterpart TW Application No. 106110126, with English Translation. (6 pages).
Office Action dated Jul. 24, 2020, issued in counterpart IN Application No. 201817035073, with English Translation. (5 pages).
Office Action dated Jan. 18, 2021, issued in counterpart KR Application No. 10-2018-7024044, with English translation (9 pages).

* cited by examiner

US 11,008,408 B2

ALKOXYMAGNESIUM, METHOD FOR PRODUCING ALKOXYMAGNESIUM, SOLID CATALYST COMPONENT FOR OLEFIN POLYMERIZATION, OLEFIN POLYMERIZATION CATALYST, AND METHOD FOR PRODUCING OLEFIN POLYMER

TECHNICAL FIELD

The present invention relates to an alkoxymagnesium, a method for producing an alkoxymagnesium, a solid catalyst component for olefin polymerization, an olefin polymerization catalyst, and a method for producing an olefin polymer.

BACKGROUND ART

As constituents of olefin polymerization catalysts, a large number of solid catalyst components for olefin polymerization that contains magnesium, titanium, an electron-donating compound, and a halogen as essential components have been suggested conventionally. Particularly, solid catalyst components prepared by using an alkoxymagnesium compound, such as diethoxymagnesium, as magnesium raw material are widely used in industries.

In a polymer obtained by polymerizing an olefin, an increase in a fine-powder polymer may inhibit a homogeneous reaction from being continued and cause process failures such as blocking of piping at the time of transferring a resulting polymer. Moreover, an increase in the particle size distribution of the resulting polymer results in an undesirable effect even on molding of the polymer. For this reason, there has been a need for a solid catalyst component with which, when an olefin is polymerized, a polymer having a small amount of a fine-powder polymer formed, a homogeneous particle diameter, and a narrow particle size distribution can be obtained.

For example, Patent Literature 1 (Japanese Patent Laid-Open No. 2005-120123) and Patent Literature 2 (Japanese Patent Laid-Open No. 2005-75995) suggest methods including treating dialkoxymagnesium powder with a polyvalent carboxylic acid halide or monocarboxylic acid halide in the presence of an inactive organic solvent to prepare a suspension containing a solid catalyst component precursor for olefin polymerization and producing a solid catalyst component for olefin polymerization using the suspension.

However, when the solid catalyst component described in Patent Literature 1 or Patent Literature 2 is used to polymerize an olefin, the amount of a fine-powder polymer to be formed may be suppressed to a certain extent, but a process for further reducing the amount to be generated has been required.

Patent Literature 3 (Japanese Patent Laid-Open No. 2004-269467) and Patent Literature 4 (Japanese Patent Laid-Open No. 2004-268909) also suggest a method including sequentially carrying out a reaction step of reacting metal magnesium with an alcohol in the presence of a catalyst to obtain a solid, a surfactant contacting step of contacting the solid with a surfactant in an inactive organic solvent to form a suspension, and a removing step of removing the solvent in the suspension to thereby prepare an alkoxymagnesium and produce a solid catalyst component for olefin polymerization using the alkoxymagnesium.

However, even when the solid catalyst component described in Patent Literature 3 or Patent Literature 4 is used to polymerize an olefin, the amount of a fine-powder polymer to be formed may be suppressed to a certain extent, but the extent of the suppression is not necessarily sufficient. Moreover, generation and mixing of many types of chemicals as byproducts in the liquid waste after production of the catalyst may make it difficult to recover and regenerate the organic solvent from the liquid waste, and adhesion of the byproducts and the like may make it difficult to operate a liquid waste regeneration facility.

Additionally, Patent Literature 5 (Japanese Patent Laid-Open No. 2008-285573) suggests a method including preparing a dialkoxymagnesium powder composition obtained by contacting a dialkoxymagnesium powder with water or a hydrate and producing a solid catalyst component for olefin polymerization using the dialkoxymagnesium powder composition.

However, when the solid catalyst component described in Patent Literature 5 is used to polymerize an olefin, the water or hydrate used for preparation of the dialkoxymagnesium powder composition may react with a halide such as a titanium halide compound used when the solid catalyst component is produced to generate hydrogen chloride as a corrosive component. Although a fine-powder polymer of 45 μm or less may be reduced to a certain extent in the resulting polymer, there has been a problem of the polymerization activity becomes lower than that of a conventional solid catalyst component because the titanium content in the solid catalyst component is extremely increased.

Furthermore, Patent Literature 6 (Japanese Patent Laid-Open No. 2007-297371) suggests large-diameter dialkoxymagnesium granules that are obtained, when a dialkoxymagnesium is synthesized by reaction of metal magnesium with an alcohol, by adjusting the ratio of the metal magnesium and the alcohol to be used to the reaction system, a method of addition, and the like, the dialkoxymagnesium granules having a spherical or ellipsoidal particle shape having an average particle diameter $D_{50}$ in the range of 60 to 200 μm, having a bulk density of 0.2 to 0.7 g/ml, having many pores therein having a pore diameter of 0.1 to 5 μm determined by TEM observation, and having a particle size distribution $(D_{90}-D_{10})/D_{50}$ of 1 or less, a method for producing the dialkoxymagnesium granules, and a method for producing a solid catalyst component for olefin polymerization using the dialkoxymagnesium granules.

However, when the dialkoxymagnesium granules described in Patent Literature 6 are used to produce a solid catalyst component for olefin polymerization, the component has a specific surface area as large as 50 to 500 m²/g. The reaction heat during production of the catalyst is high, and there has been a problem in that particles that have locally generated heat partially disintegrate to thereby become likely to form fine-powder dialkoxymagnesium.

CITATION LIST

Patent Literature

[Patent Literature 1] Japanese Patent Laid-Open No. 2005-120123
[Patent Literature 2] Japanese Patent Laid-Open No. 2005-75995
[Patent Literature 3] Japanese Patent Laid-Open No. 2004-269467
[Patent Literature 4] Japanese Patent Laid-Open No. 2004-268909
[Patent Literature 5] Japanese Patent Laid-Open No. 2008-285573

[Patent Literature 6] Japanese Patent Laid-Open No. 2007-297371

SUMMARY OF INVENTION

Advantageous Effect of Invention

Under such circumstances, it is an object of the present invention to provide a novel alkoxymagnesium which, when used as a constituent of a solid catalyst component for olefin polymerization to polymerize an olefin, may reduce the formation rate of a fine powder and form a polymer having an excellent particle size distribution under high polymerization activity as well as to provide a method for producing the alkoxymagnesium, a solid catalyst component for olefin polymerization, an olefin polymerization catalyst, and a method for producing an olefin polymer.

DESCRIPTION OF EMBODIMENTS

The present inventors have conducted extensive studies in order to solve the above technical problem. Alkoxymagnesiums are formed of secondary particles each of which is an aggregate of primary particles, and a conventional alkoxymagnesium contains more than 3% by mass of a fine powder (particles having a particle diameter of 5 μm or less) formed exclusively by disintegrated secondary particles, based on the total particle mass. The present inventors have found that this fine-powder alkoxymagnesium is likely to form a fine-powder polymer when an olefin is polymerized.

The present inventors have conducted further investigations based on this finding and have found that the problem described above may be solved by an alkoxymagnesium that is composed of secondary particles each of which is an aggregate of primary particles having an average particle diameter of less than 1 μm and that has a ratio of the average particle diameter of the primary particles/the average particle diameter of the secondary particles of 0.1 or less, a total pore volume of 0.5 to 1 cm$^3$/g, a specific surface area of less than 50 m$^2$/g, and a particle size distribution index (SPAN) of 1 or less, having completed the present invention.

That is, the present invention provides the following:
(1) An alkoxymagnesium comprising secondary particles each of which is an aggregate of primary particles having an average particle diameter of less than 1 μm, wherein
a ratio of an average particle diameter of the primary particles/an average particle diameter of the secondary particles is 0.1 or less,
a total pore volume is 0.5 to 1 cm$^3$/g, a specific surface area is less than 50 m$^2$/g, and a particle size distribution index (SPAN) is 1 or less,
(2) The alkoxymagnesium according to (1), wherein a content of a fine powder having a particle diameter of 5 μm or less is 3% by mass or less based on a total particle mass, the total pore volume is 0.5 to 1 cm$^3$/g, and 50% or more of pores having a pore diameter of 1 μm or less has a pore diameter of 0.5 μm or less,
(3) The alkoxymagnesium according to (1) or (2), wherein the average particle diameter of the secondary particles is less than 60 μm,
(4) A method for producing an alkoxymagnesium, including sequentially carrying out
a solid formation step of reacting metal magnesium with an alcohol in the presence of a catalyst to form a solid, and
a contact step of contacting the solid with one or more carboxylic acid esters in an organic solvent to form a suspension, (5) The method for producing an alkoxymagnesium according to (4), wherein the alcohol is one or more selected from methanol, ethanol, n-propanol, isopropanol, n-butanol, isobutanol, and 2-ethylhexyl alcohol,
(6) The method for producing an alkoxymagnesium according to (4) or (5), wherein the organic solvent is one or more selected from aliphatic hydrocarbon compounds and aromatic hydrocarbon compounds,
(7) The method for producing an alkoxymagnesium according to any of (4) to (6), wherein
the carboxylic acid ester is one or more selected from compounds represented by the following general formula (I);

[Formula 1]

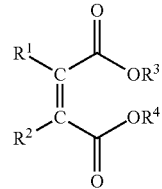

(I)

wherein $R^1$ and $R^2$ each are a hydrogen atom, a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, $R^1$ and $R^2$ may be identical or different from each other or $R^1$ and $R^2$ may bond with each other to form a ring, and $R^3$ and $R^4$ each are an alkyl group having 1 to 12 carbon atoms and may be identical or different from each other,
compounds represented by the following general formula (II);

[Formula 2]

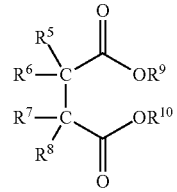

(II)

wherein $R^5$ to $R^8$ each represent a hydrogen atom, a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, $R^5$ to $R^8$ may be identical or different from one another, and $R^5$ and $R^6$, and $R^7$ and $R^8$ may bond with each other to form a ring, and $R^9$ and $R^{10}$ each are an alkyl group having 1 to 12 carbon atoms and may be identical or different from each other, and compounds represented by the following general formula (III);

[Formula 3]

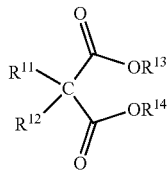
(III)

wherein $R^{11}$ and $R^{12}$ each represent a hydrogen atom, a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, $R^{11}$ and $R^{12}$ may be identical or different from each other or $R^{11}$ and $R^{12}$ may bond with each other to form a ring, and $R^{13}$ and $R^{14}$ each are an alkyl group having 1 to 12 carbon atoms and may be identical or different, (8) The method for producing an alkoxymagnesium according to any of (4) to (7), wherein the carboxylic acid ester is one or more selected from diethyl succinate, dibutyl succinate, bis(2-ethylhexyl) succinate, diethyl maleate, dibutyl maleate, bis(2-ethylhexyl) maleate, diethyl malonate, dibutyl malonate, and bis(2-ethylhexyl) malonate, (9) The method for producing an alkoxymagnesium according to any of (4) to (8), wherein the alkoxymagnesium is diethoxymagnesium,

(10) The method for producing an alkoxymagnesium according to any of (4) to (9), wherein, by carrying out the contact step, a portion of the solid is reacted with, the carboxylic acid ester to form a reactant, a portion of the solid is dissolved in a mixture of the carboxylic acid ester and the organic solvent, or a portion of the solid is liberated in a mixture of the carboxylic acid ester and the organic solvent,

(11) A solid catalyst component for olefin polymerization obtained by contacting (a) the alkoxymagnesium according to any one of (1) to (3), (b) a titanium halogen compound, and (c) an electron-donating compound with one another,

(12) An olefin polymerization catalyst including
(A) the solid catalyst component for olefin polymerization according to (11), (B) an organoaluminum compound represented by the following general formula (IV);

(IV)

wherein $R^{15}$ represents an alkyl group having 1 to 4 carbon atoms, Q represents a hydrogen atom or halogen atom, and p is a real number satisfying $0<p\leq3$, provided that, when a plurality of $R^{15}$ are present, each $R^{15}$ may be identical or different from one another and when a plurality of Q are present, each Q may be identical or different from one another, and (C) an external electron-donating compound,

(13) The olefin polymerization catalyst according to (12), wherein
(C) the external electron-donating compound is one or more selected from organosilicon compounds represented by the following general formula (V);

(V)

wherein $R^{16}$ represents an alkyl group having 1 to 12 carbon atoms, a vinyl group, an alkenyl group having 3 to 12 carbon atoms, a cycloalkyl group having 3 to 12 carbon atoms, a cycloalkenyl group having 3 to 12 carbon atoms, an aromatic hydrocarbon group having 6 to 15 carbon atoms, or an aromatic hydrocarbon group having 6 to 15 carbon atoms and having a substituent, provided that, when a plurality of $R^{16}$ are present, the plurality of $R^{16}$ may be identical or different from one another, $R^{17}$ represents an alkyl group having 1 to 4 carbon atoms, a vinyl group, an alkenyl group having 3 to 12 carbon atoms, a cycloalkyl group having 3 to 6 carbon atoms, an aromatic hydrocarbon group having 6 to 12 carbon atoms, or an aromatic hydrocarbon group having 7 to 12 carbon atoms and having a substituent, provided that, when a plurality of $R^{17}$ are present, the plurality of $R^{17}$ may be identical or different from one another, and q is an integer satisfying $0\leq q\leq3$, and aminosilane compounds represented by the general formula (VI);

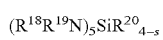
(VI)

wherein $R^{18}$ and $R^{19}$ each represent a hydrogen atom, an alkyl group having 1 to 20 carbon atoms, a vinyl group, an alkenyl group having 3 to 20 carbon atoms, a cycloalkyl group having 3 to 20 carbon atoms, a cycloalkenyl group having 3 to 20 carbon atoms, or an aryl group having 6 to 20 carbon atoms, $R^{18}$ and $R^{19}$ may be identical or different from each other or may bond with each other to form a ring, and when a plurality of $R^{18}R^{19}N$ groups are present, the plurality of $R^{18}R^{19}N$ groups may be identical or different from one another, $R^{20}$ represents an alkyl group having 1 to 20 carbon atoms, a vinyl group, an alkenyl group having 3 to 12 carbon atoms, an alkoxy group having 1 to 20 carbon atoms, a vinyloxy group, an alkenyloxy group having 3 to 20 carbon atoms, a cycloalkyl group having 3 to 20 carbon atoms, a cycloalkyloxy group having 3 to 20 carbon atoms, an aryl group having 6 to 20 carbon atoms, or an aryloxy group having 6 to 20 carbon atoms, provided that, when a plurality of $R^{20}$ are present, the plurality of $R^{20}$ may be identical or different from one another, and s is an integer of 1 to 3,

(14) A method for producing an olefin polymer including polymerizing an olefin in the presence of the olefin polymerization catalyst according to (12) or (13).

Advantageous Effect of Invention

According to the present invention, it is possible to provide a novel alkoxymagnesium which, when used as a constituent of a solid catalyst component for olefin polymerization to polymerize an olefin, may reduce the formation rate of a fine powder and form a polymer having an excellent particle size distribution under high polymerization activity as well as to provide a method for producing the alkoxymagnesium, a solid catalyst component for olefin polymerization, an olefin polymerization catalyst, and a method for producing an olefin polymer.

DESCRIPTION OF EMBODIMENT

Figure 1:
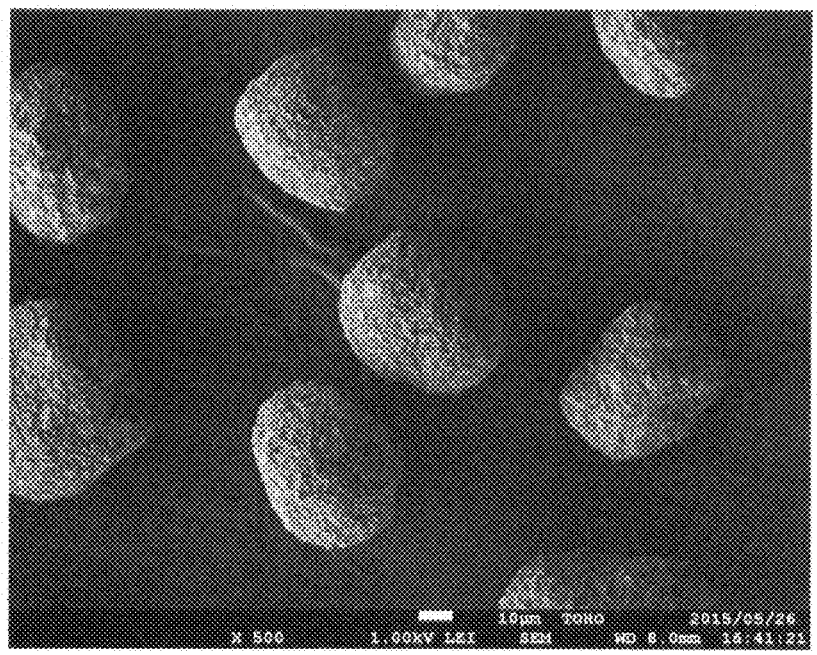
FIG. 1 shows the appearance shape of an alkoxymagnesium obtained in an Example of the present invention.

An alkoxymagnesium according to the present invention is composed of secondary particles each of which is an aggregate of primary particles having an average particle diameter of less than 1 μm, wherein the ratio represented by the average particle diameter of the primary particles/the average particle diameter of the secondary particles is 0.1 or less, the total pore volume is 0.5 to 1 cm$^3$/g, the specific surface area is less than 50 m$^2$/g, and the particle size distribution index (SPAN) is 1 or less.

The alkoxymagnesium according to the present invention is composed of secondary particles each of which is an aggregate of primary particles.

In the alkoxymagnesium according to the present invention, the average particle diameter of the primary particles is less than 1 μm, preferably 0.2 μm to 0.9 μm, more preferably 0.3 μm to 0.9 μm.

In the alkoxymagnesium according to the present invention, the average particle diameter of the secondary particles is preferably less than 60 μm, more preferably 10 μm or more and less than 60 μm, more preferably 15 μm or more and less than 60 μm.

The alkoxymagnesium according to the present invention, which is composed of secondary particles each of which is an aggregate of primary particles, when used as a constituent of a solid catalyst component for olefin polymerization to polymerize an olefin, can suitably suppress formation of a fine-powder polymer.

The particle diameter of conventional primary particles is as large as 1 to 10 μm, and primary particles coming off from the secondary particle surface have been one of the causes for formation of a fine-powder polymer. Meanwhile, the alkoxymagnesium according to the present invention includes primary particles having a particle diameter of as small as less than 1 μm. Primary particles floating during washing in the process of producing a solid catalyst component may be easily extracted into effluent, and thus, it is conceived that the amount of a fine-powder polymer olefin may be reduced when an olefin is polymerized.

The alkoxymagnesium according to the present invention has a ratio represented by the average particle diameter of the primary particles constituting the alkoxymagnesium/the average particle diameter of the secondary particles constituting the alkoxymagnesium is 0.1 or less, preferably 0.001 to 0.08, more preferably 0.005 to 0.05.

In the alkoxymagnesium according to the present invention, the ratio of the average particle the diameter of the primary particles/the average particle diameter of the secondary particles is 0.1 or less, and thus, the secondary particles have sufficiently grown relative to the primary particles. When used as a constituent of a solid catalyst component for olefin polymerization to polymerize an olefin, the alkoxymagnesium can suitably suppress formation of a fine-powder polymer.

In the present application, the average particle diameter of the primary particles of the alkoxymagnesium means the average particle diameter obtained by visual measurement of a negative resulted from photographing by a scanning electron microscope for the longest diameter of 100 or more particles and calculation by a statistical analysis approach based on the longest diameter obtained.

The average particle diameter of the alkoxymagnesium secondary particles means the average particle diameter $D_{50}$ (particle diameter corresponding to the 50% cumulative particle size in the volumetric cumulative particle size distribution) when one hundred thousand or more each of measurement samples in a dry state are measured using a laser-diffraction particle size distribution analyzer that supports dry dispersion.

In the alkoxymagnesium according to the present invention, the content of fine powder, that is, particles having a particle diameter of 5 μm or less, is preferably 3% by mass or less based on the total particle mass, more preferably 2% by mass or less based on the total particle mass, still more preferably 1% by mass or less based on the total particle mass.

The fine powder described above is formed exclusively from disintegration of the secondary particles of the alkoxymagnesium, but primary particles and the like, which do not constitute the secondary particles, shall be included in the fine powder, as long as their particle diameter satisfies the definition described above.

The alkoxymagnesium according to the present invention, when having a content of a fine powder having a particle diameter of 5 μm or less of 3% by mass or less based on the total particle mass, makes it possible to easily obtain a polymer having a particle diameter of 75 μm or less with a sufficiently reduced amount of a polymer fine powder while maintaining a high yield of a polymer obtained when an olefin is polymerized, and thus, can stably provide a general-purpose polyolefin at a lower cost.

The particle size distribution of the secondary particles of the alkoxymagnesium according to the present invention has a particle size distribution index (SPAN) of 1.0 or less, preferably 0.8 or less. The SPAN is represented by $(D_{90}-D_{10})/D_{50}$, where $D_{90}$ is a particle diameter corresponding to the 90% cumulative particle size in the volumetric cumulative particle size distribution, $D_{50}$ is a particle diameter corresponding to the 50% cumulative particle size in the volumetric cumulative particle size distribution (average particle diameter), and $D_{10}$ is a particle diameter corresponding to the 10% cumulative particle size in the volumetric cumulative particle size distribution.

In the present application, the content ratio of a fine powder having a particle diameter of 5 μm or less means a value obtained by measurement with by a laser-diffraction particle size distribution analyzer that supports dry dispersion (Mastersizer 3000 manufactured by Malvern Panalytical Ltd). $D_{93}$, $D_{50}$, and $D_{10}$ of the secondary particles constituting the alkoxymagnesium respectively mean a particle diameter corresponding to the 90%, 50%, and 10% cumulative particle size in the volumetric cumulative particle size distribution when measured using a laser light scattering diffraction particle size analyzer.

The form of the secondary particles of the alkoxymagnesium according to the present invention is not particularly limited, and is a granular form or powder form in a dry state. The shape thereof is usually spherical, but not necessarily true-spherical, and may be similar-spherical, such as elliptical or potato-shaped. Specifically, the secondary particles have a ratio between the long axis diameter l and the short axis diameter w of the secondary particles (l/w) of preferably 3 or less, more preferably 1 to 2, still more preferably 1 to 1.5.

The alkoxymagnesium according to the present invention, when measured by mercury porosimetry, has a pore diameter of 50% or more of pores having a pore diameter of 1 μm or less (pore diameter of more than a half of pores having a pore diameter of 1 μM or less) of preferably 0.5 μm or less, more preferably 0.05 to 0.5 μm, still more preferably 0.1 to 0.5 μm.

The alkoxymagnesium according to the present invention, when measured by mercury porosimetry, has a total pore volume of 0.5 to 1 cm$^3$/g, preferably 0.55 to 0.9 cm$^3$/g, more preferably 0.6 to 0.8 cm$^3$/g.

The alkoxymagnesium according to the present invention has a pore diameter or total pore volume of 50% or more of pores having a pore diameter of 1 μm or less within the range described above. Thus, when used as a constituent of a solid catalyst component for olefin polymerization to polymerize propylene with ethylene, for example, the alkoxymagnesium retains a rubber component constituted by the copolymer in its pores to suppress elution of the rubber component to the particle surface, suppresses sticking among the copolymer particles and adhesion of the copolymer to inside the reactor, and can exhibit satisfactory particle flowability.

In the present application, the pore diameter distribution and pore volume of the alkoxymagnesium mean values obtained by mercury porosimetry using an AutoPore III 9400 series automated mercury porosimeter manufactured by SHIMADZU CORPORATION.

The alkoxymagnesium according to the present invention has a specific surface area of less than 50 $m^2/g$, preferably 5 $m^2/g$ to 40 $m^2/g$ or less, more preferably 10 $m^2/g$ to 30 $m^2/g$.

In the present application, the specific surface area of the alkoxymagnesium means a value obtained by automatically measuring a measurement sample, which has been vacuum-dried at 50° C. for two hours in advance, using a mixture gas of nitrogen and helium, by means of an automatic surface area analyzer HM model-1230 manufactured by Mountech Co., Ltd. in accordance with the BET method.

The alkoxymagnesium according to the present invention has a bulk density of preferably 0.25 to 0.50 g/ml, more preferably 0.26 to 0.40 g/ml, still more preferably 0.28 to 0.35 g/ml.

In the present application, the bulk density of the alkoxymagnesium means a value measured in accordance with the definition of JIS K6721.

The alkoxymagnesium according to the present invention, which is composed of secondary particles each of which is constituted by aggregates of primary particles, generally has a larger specific surface area compared with alkoxymagnesiums produced by a spray dry method or the like, and is likely to have the bulk density described above because of its large pore volume.

Since the alkoxymagnesium according to the present invention has a large specific surface area and a large pore volume, when a solid catalyst component prepared using the alkoxymagnesium is used in polymerization of an olefin, a polymer having excellent particle properties can be obtained at a high yield. Furthermore, in block polymerization, a copolymer having excellent particle properties can be obtained at a high yield, even when the ratio of a rubber-like polymer formed is high.

Examples of the alkoxymagnesium according to the present invention include one or more selected from diethoxymagnesium, dipropoxymagnesium, dibutoxymagnesium, dipentoxymagnesium, diisooctoxymagnesium, ethoxybutoxymagnesium, and ethoxyisooctoxymagnesium, and the alkoxymagnesium is preferably diethoxymagnesium.

According to the present invention, it is possible to provide a novel alkoxymagnesium which, when used as a constituent of a solid catalyst component for olefin polymerization to polymerize an olefin, may reduce the formation rate of a fine powder and form a polymer having an excellent particle size distribution under high polymerization activity.

Particularly, the alkoxymagnesium according to the present invention, when used as a constituent of a solid catalyst component for olefin polymerization, makes it possible to obtain an olefin polymer powder having a better particle shape and a narrow particle size distribution, can improve the handling operability of the polymer powder formed at the time of polymerization operation, and can suitably suppress occurrence of clogging or the like caused by a fine powder contained in the polymer powder formed.

Next, the method for producing an alkoxymagnesium according to the present invention will be described.

The method for producing an alkoxymagnesium according to the present invention is characterized by sequentially carrying out a solid formation step of reacting metal magnesium with an alcohol in the presence of a catalyst to form a solid, and a contact step of contacting the solid with one or more carboxylic acid esters in an organic solvent to form a suspension.

In the method for producing an alkoxymagnesium according to the present invention, the metal magnesium used in the solid formation step is preferably one of a several ten to several hundred meshes, specifically of about 100 meshes, and powder magnesium having good reactivity is preferable.

In the method for producing an alkoxymagnesium according to the present invention, examples of the alcohol to react with the metal magnesium used in the solid formation step include one or more selected from methanol, ethanol, n-propanol, isopropanol, n-butanol, isobutanol, and 2-ethylhexyl alcohol, and ethanol is preferable.

The alcohols described above are preferably ones from which moisture is sufficiently removed before contacted with the metal magnesium for reaction.

Examples of the catalyst subjected to the reaction of the metal magnesium and alcohol include one or more selected from halogenated alkyls such as methyl bromide, methyl chloride, ethyl bromide, and ethyl chloride, halogenated metals such as magnesium chloride and aluminum chloride, dialkoxymagnesiums such as diethoxymagnesium, iodine, and acetic acid esters. Of these, particularly, one or more selected from iodine and diethoxymagnesium are preferable.

The catalyst is preferably added to the reaction system in the early stage of the solid formation step.

The metal magnesium and the alcohol are contacted with each other so as to achieve a mass ratio represented by metal magnesium/alcohol of preferably 1/2 to 1/30, more preferably 1/5 to 1/20, still more preferably 1/9 to 1/15.

The metal magnesium and the alcohol can be reacted with each other by a known method.

An exemplary method can be a method in which the metal magnesium and the alcohol are added continuously or intermittently to a reaction system containing the catalyst such that the mass ratio above described is achieved in the end to be brought in contact and reacted with each other, and then, the reactant is retained under reflux of the alcohol to be subjected to aging reaction.

The reaction time for the metal magnesium and the alcohol is preferably 5 to 80 minutes, and the aging time is preferably 1 to 30 hours.

The solid obtained as described above may be subjected to the next step, still as a suspension including the alcohol as the solvent or in a dry state with moisture removed.

In the method for producing an alkoxymagnesium according to the present invention, the solid obtained in the solid formation step and one or more carboxylic acid esters are subjected to the contact step, where the solid and ester(s) are contacted with each other in an organic solvent to form a suspension.

The carboxylic acid ester is preferably an aliphatic carboxylic acid ester, and is more preferably one or more selected from compounds represented by the following general formula (I):

[Formula 4]

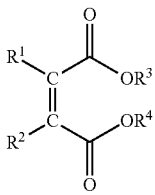

(I)

wherein $R^1$ and $R^2$ each are a hydrogen atom, a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, $R^1$ and $R^2$ may be identical or different from each other or $R^1$ and $R^2$ may bond with each other to form a ring, and $R^3$ and $R^4$ each are an alkyl group having 1 to 12 carbon atoms and may be identical or different from each other, compounds represented by the following general formula (II);

[Formula 5]

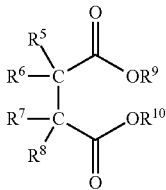

(II)

wherein $R^5$ to $R^8$ each represent a hydrogen atom, a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, $R^5$ to $R^8$ may be identical or different from one another, and $R^5$ and $R^6$, and $R^7$ and $R^8$ may bond with each other to form a ring, and $R^9$ and $R^{10}$ each are an alkyl group having 1 to 12 carbon atoms and may be identical or different from each other, and compounds represented by the following general formula (III);

[Formula 6]

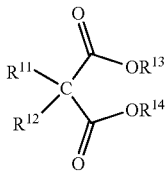

(III)

wherein $R^{11}$ and $R^{12}$ each represent a hydrogen atom, a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, $R^{11}$ and $R^{12}$ may be identical or different from each other or $R^{11}$ and $R^{12}$ may bond with each other to form a ring, and $R^{13}$ and $R^{14}$ each are an alkyl group having 1 to 12 carbon atoms and may be identical or different.

When the carboxylic acid ester is a compound represented by the following general formula (I);

[Formula 7]

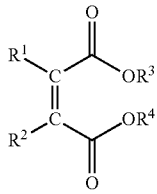

(I)

$R^1$ and $R^2$ each are a hydrogen atom, a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or atoms, a cycloalkyl group having 3 to 12 carbon atoms, or an aromatic hydrocarbon group having 6 to 20 carbon atoms, $R^1$ and $R^2$ may be identical or different from each other or $R^1$ and $R^2$ may bond with each other to form a ring, and $R^3$ and $R^4$ each are an alkyl group having 1 to 12 carbon atoms and may be identical or different from each other.

$R^3$ and $R^4$ each are preferably an alkyl group having 4 to 12 carbon atoms, more preferably an alkyl group having 7 to 12 carbon atoms.

Specific examples of the carboxylic acid ester represented by the general formula (I) can include one or more selected from maleic acid diesters in which $R^1$ and $R^2$ each are a hydrogen atom, alkylmaleic acid diesters in which $R^1$ is a hydrogen atom and $R^2$ is a straight-chain alkyl group having 1 to 12 carbon atoms, a branched-chain alkyl group having 3 to 12 carbon atoms, vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, dialkylmaleic acid diesters in which $R^1$ and $R^2$ are each independently a group selected from a straight-chain alkyl group having 1 to 12 carbon atoms, a branched alkyl group having 3 to 12 carbon atoms, a vinyl group, a straight-chain alkenyl alkenyl group having 3 to 12 carbon atoms, a cycloalkyl group having 3 to 12 carbon atoms, or an aromatic hydrocarbon group having 6 to 20 carbon atoms, cycloalkylmaleic acid diesters in which at least one of $R^1$ and $R^2$ is a cycloalkyl group having 3 to 12 carbon atoms, and the like, and among the carboxylic acid esters described above, diethyl maleate, dibutyl maleate, or bis(2-ethylhexyl) maleate is particularly preferable.

When the carboxylic acid ester is a compound represented by the following general formula (II);

[Formula 8]

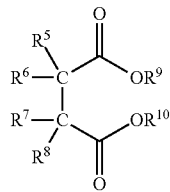

(II)

$R^5$ to $R^8$ each represent a hydrogen atom, a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, $R^5$ to $R^8$ may be identical or different from one another, and $R^5$ and $R^6$, and $R^7$ and $R^8$ may bond with each another, and $R^5$ and $R^6$, and $R^7$ and $R^8$ may bond with each other to form a ring. $R^9$ and $R^{10}$ each are an alkyl group having 1 to 12 carbon atoms and may be identical or different from each other.

$R^9$ and $R^{10}$ each are preferably an alkyl group having 4 to 12 carbon atoms, more preferably an alkyl group having 7 to 12 carbon atoms.

Specific examples of the carboxylic acid ester represented by the general formula (II) include one or more selected from succinic acid diesters in which $R^5$ to $R^8$ each are a hydrogen atom, alkylsuccinic acid diesters in which $R^5$ to $R^7$ each are a hydrogen atom, $R^8$ is a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, succinic acid diesters having a plurality of alkyl groups in which $R^5$ to $R^8$ are each independently a group selected from a straight-chain alkyl group having 1 to 12 carbon atoms, a branched alkyl group having 3 to 12 carbon atoms, a vinyl group, a straight-chain alkenyl group or a branched alkenyl group having 3 to 12 carbon atoms, a cycloalkyl group having 3 to 12 carbon atoms, and an aromatic hydrocarbon group having 3 to 12 carbon atoms, and an aromatic hydrocarbon group having 6 to 20 carbon atoms diesters in which at least one of $R^5$ to $R^8$ is one or more selected from cycloalkyl groups having 3 to 12 carbon atoms, and among the carboxylic acid esters described above, diethyl succinate, dibutyl succinate, or bis(2-ethylhexyl) succinate is particularly preferable.

When the carboxylic acid ester is a compound represented by the following general formula (III);

[Formula 9]

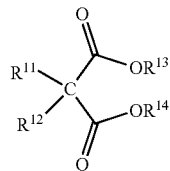

(III)

$R^{11}$ and $R^{12}$ each represent a hydrogen atom, a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, $R^{11}$ and $R^{12}$ may be identical or different from each other, and $R^{11}$ and $R^{12}$ may bond with each other to form a ring. $R^{13}$ and $R^{14}$ each are an alkyl group having 1 to 12 carbon atoms and may be identical or different.

$R^{13}$ and $R^{14}$ each are preferably an alkyl group having 4 to 12 carbon atoms, more preferably an alkyl group having 7 to 12 carbon atoms.

Specific examples of the carboxylic acid ester represented by the general formula (III) can include one or more selected from malonic acid diesters in which $R^{11}$ and $R^{12}$ each are a hydrogen atom, alkylmalonic acid diesters in which $R^{11}$ is a hydrogen atom, $R^{12}$ is a straight-chain alkyl group having 1 to 12 carbon atoms, a branched-chain alkyl group having 3 to 12 carbon atoms, vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, dialkylmalonic acid diesters in which $R^{11}$ and $R^{12}$ are each independently a group selected from a straight-chain alkyl group having 1 to 12 carbon atoms, a branched-chain alkyl group having 3 to 12 carbon atoms, a vinyl group, a straight-chain alkenyl group having 3 to 12 carbon atoms, a branched-chain alkenyl group having 3 to 12 carbon atoms, a cycloalkyl group having 3 to 12 carbon atoms, or an aromatic hydrocarbon group having 6 to 20 carbon atoms, and cycloalkylmalonic acid diesters in which at least one of $R^{11}$ and $R^{12}$ is one or more selected from cycloalkyl groups having 3 to 12 carbon atoms, and among the carboxylic acid esters described above, diethyl malonate, dibutyl malonate, or bis(2-ethylhexyl) malonate is particularly preferable.

One of the carboxylic acid esters described above may be used singly or two or more of these may be used in combination.

In the method for producing an alkoxymagnesium according to the present invention, in the contact step, the solid and the carboxylic acid ester described above are contacted with each other in an organic solvent to form a suspension.

The organic solvent described above is suitably one that dissolves carboxylic acid esters and does not dissolve a solid (magnesium compound), and specific examples thereof can include one or more selected from aliphatic hydrocarbon compounds such as pentane, hexane, heptane, octane, nonane, decane, and cyclohexane, aromatic hydrocarbon compounds such as benzene, toluene, xylene, and ethylbenzene, halogenated hydrocarbon compounds such as methylene chloride and 1,2-dichlorobenzene, alcohols such as methanol, ethanol, and isooctyl alcohols, and ethers such as diethyl ether. Among these, one or more selected from hydrocarbon compounds such as heptane, toluene, and xylene are preferable.

In the method for producing an alkoxymagnesium according to the present invention, the amount of contact between the solid and carboxylic acid ester described above, when the solid and the carboxylic acid ester are contacted with each other in an organic solvent, is preferably 0.1 mmol or more of the carboxylic acid ester, more preferably 0.3 to 60 mmol of the carboxylic acid ester, still more preferably 0.5 to 50 mmol of the carboxylic acid ester, even more preferably 0.5 to 30 mmol of the carboxylic acid ester, based on one gram of the solid.

In the contact step of the method for producing an alkoxymagnesium according to the present invention, the amount of the organic solvent used is preferably 0.1 to 50 ml, more preferably 1 to 30 ml, still more preferably 2 to 10 ml based on one gram of the solid.

In the method for producing an alkoxymagnesium according to the present invention, the contact temperature between the solid and the carboxylic acid ester in the organic solvent is preferably −20 to 150° C., more preferably 10 to 130° C., still more preferably 50 to 110° C. The contact time between the solid and the carboxylic acid ester in the organic solvent is preferably 1 minute to 50 hours, more preferably 5 minutes to 30 hours, still preferably 10 minutes to 10 hours.

In the method for producing an alkoxymagnesium according to the present invention, the solid obtained in the solid formation step and one or more carboxylic acid esters are contacted with each other in an organic solvent to form a suspension in the contact step.

In the method for producing an alkoxymagnesium according to the present invention, it is conceived that carrying out the contact step reacts a portion of the solid with the carboxylic acid ester to form a reactant, dissolves a portion of the solid in the mixture of the carboxylic acid ester and the organic solvent, or liberates a portion of the solid in the mixture of the carboxylic acid ester and the organic solvent.

In other words, in the method for producing an alkoxymagnesium according to the present invention, it is conceived that, by contacting the solid obtained in the solid formation step with the carboxylic acid ester in the contact step, (1) at least a portion of the fine-powder dialkoxymagnesium adhering to the alkoxymagnesium reacts with the carboxylic acid ester to form a reactant by action such as occurrence of so-called "transesterification", in which the alkyl chain of the alkoxy group constituting the dialkoxymagnesium and the alkyl chain of the ester residue constituting the carboxylic acid diester are exchanged with each other, and then, the reactant can be easily removed, (2) at least a portion of the fine powder adhering to the alkoxymagnesium is dissolved in the mixture of the carboxylic acid ester and the organic solvent and then, the dissolved powder can be easily removed, or (3) at least a portion of fine powder adhering to the alkoxymagnesium is easily liberated by effects such as an antistatic effect and the liberated powder can be easily removed by washing treatment and the like.

Contacting the solid obtained in the solid formation step with the carboxylic acid ester in the contact step increases the smoothness of the solid particle surface. Use of these particles in preparation of a solid catalyst component for olefin polymerization facilitates uniform reaction to thereby enable formation of aggregates to be suppressed.

When the aggregates described above (aggregated solid catalyst component) are used to polymerize an olefin to form a polymer, the aggregate particles disintegrate to be likely to form a fine-powder. In the method for producing an alkoxymagnesium according to the present invention, as aforementioned, contacting the solid obtained in the solid formation step with the carboxylic acid ester in the contact step can suitably suppress formation of a fine-powder polymer derived from the aggregate particles.

In the method for producing an alkoxymagnesium according to the present invention, removal treatment of removing the solvent from the reaction liquid may be further carried out after the contact step.

The removal treatment is preferably carried out by removing the solvent from the suspension by decantation, filtration, or the like.

The removal treatment can remove the carboxylic acid ester remaining in the reaction liquid obtained in the solid formation step and the alkoxymagnesium partially dissolved in the reaction liquid to thereby improve the purity of the alkoxymagnesium to be obtained.

In the method for producing an alkoxymagnesium according to the present invention, the alkoxymagnesium may be further treated with an organic solvent or the like after the removal treatment, and such treatment with an organic solvent can wash off and remove excessive carboxylic acid ester contained in the residue (reaction product) obtained after the removal treatment.

The details of the alkoxymagnesium to be obtained by the production method of the present invention are as detailed in the description of the alkoxymagnesium according to the present invention.

According to the present invention, it is possible to provide a method for easily producing a novel alkoxymagnesium which, when used as a constituent of a solid catalyst component for olefin polymerization to polymerize an olefin, may reduce the formation rate of a fine powder and form a polymer having an excellent particle size distribution under high polymerization activity.

Next, the solid catalyst component for olefin polymerization according to the present invention will be described.

The solid catalyst component for olefin polymerization according to the present invention is characterized by being prepared by contacting the alkoxymagnesium according to the present invention (a), a titanium halide compound (b), and an electron-donating compound (c) with one another.

The details of the alkoxymagnesium to be produced by the production method of the present invention are as aforementioned.

When an alkoxymagnesium produced by the production method according to the present invention is used as the alkoxymagnesium according to the present invention, the alkoxymagnesium, still as a suspension with the organic solvent used in the contact step or in a separated or dried state as required, is used as a constituent of the solid catalyst component for olefin polymerization.

When an alkoxymagnesium produced by the production method according to the present invention is used as the alkoxymagnesium constituting the solid catalyst component for olefin polymerization according to the present invention, in view of simplification of the step for producing the solid catalyst component, ones in the form of suspension, which require no separation and drying treatments, are desired. When the organic solvent is a solvent reactive with the titanium halide compound (b), such as an alcohol or ether, it is preferred that the organic solvent be sufficiently removed by drying the suspension under vacuum or under heating.

Examples of the titanium halide compound (b) constituting the solid catalyst component for olefin polymerization according to the present invention can include one or more selected from known compounds. Tetravalent titanium halide compounds are preferable, and titanium tetrachloride is more preferable.

Examples of the electron-donating compound (c) constituting the solid catalyst component for olefin polymerization according to the present invention can include one or more selected from known compounds. Compounds having an oxygen atom or nitrogen atom are preferable.

The electron-donating compound (c) is preferably one or more selected from succinic acid esters, maleic acid esters, cyclohexanecarboxylic acid esters, ethercarboxylic acid esters, dicarbonates, and ethercarbonates.

In the solid catalyst component for olefin polymerization according to the present invention, the content of each of titanium atoms, magnesium atoms, halogen atoms, and the electron-donating compound is not particularly limited.

In the solid catalyst component for olefin polymerization according to the present invention, the content ratio of titanium atoms is preferably 1.8 to 8.0% by mass, more preferably 2.0 to 8.0% by mass, still more preferably 3.0 to 8.0% by mass.

In the solid catalyst component for olefin polymerization according to the present invention, the content ratio of magnesium atoms is preferably 10 to 70% by mass, more preferably 10 to 50% by mass, still more preferably 15 to 40% by mass, even more preferably 15 to 25% by mass.

In the solid catalyst component for olefin polymerization according to the present invention, the content ratio of halogen atoms is preferably 20 to 90% by mass, more preferably 30 to 85% by mass, still more preferably 40 to 80% by mass, even more preferably 45 to 75% by mass.

In the solid catalyst component for olefin polymerization according to the present invention, the content ratio of the electron-donating compound (c) in total is preferably 0.5 to 30% by mass, more preferably 1 to 25% by mass, still more preferably 2 to 20% by mass.

In the solid catalyst component for olefin polymerization according to the present invention, in order for the component to exert its total performance in good balance, it is desirable that the titanium content be 3 to 8% by mass, the magnesium content be 15 to 25% by mass, the content of halogen atoms be 45 to 75% by mass, and the content of the electron-donating compound (c) be 2 to 20% by mass.

An example of the method for preparing the solid catalyst component for olefin polymerization according to the present invention is a method including contacting the alkoxymagnesium (a), the titanium halide compound (b), and the electron-donating compound (c) with one another in the presence of an inert organic solvent having a boiling point of 50 to 150° C. (d).

Examples of the inert organic solvent having a melting point of 50 to 150° C. (d) can include one or more selected from toluene, xylene, ethylbenzene, heptane, octane, and decane.

As the inert organic solvent having a melting point of 50 to 150° C., aromatic hydrocarbon compounds and aliphatic hydrocarbon compounds are prevalent. Unless the reactivity and the solubility of impurities after washing are reduced, inert organic solvents other than aromatic hydrocarbons and aliphatic hydrocarbons may be used.

When the solid catalyst component for olefin polymerization according to the present invention is prepared, a polysiloxane may be further added to the reaction system. Such a polysiloxane may be selected from polysiloxanes conventionally known. One or more selected from decamethylcyclopentasiloxane and dimethylpolysiloxane are preferable, and decamethylcyclopentasiloxane is more preferable.

The details of the method for preparing a solid catalyst component for olefin polymerization according to the present invention are the same as those of methods for preparing a solid catalyst component for olefin polymerization conventionally known.

As aforementioned, the solid catalyst component for olefin polymerization according to the present invention is obtained by contacting the alkoxymagnesium according to the present invention (a), the titanium halide compound (b), and the electron-donating compound (c) with one another to react the components with one another. In the present art, it is difficult to identify the solid catalyst component for olefin polymerization from their structure and physical properties. Thus, that the component has to be identified with a so-called product by process form has been the common general knowledge of those skilled in the art. Accordingly, herein, even if the solid catalyst component for olefin polymerization is defined with a so-called product by process form, it is clear that its content is obvious.

According to the present invention, it is possible to provide a solid catalyst component for olefin polymerization which may reduce the formation rate of a fine powder and form a polymer having an excellent particle size distribution under high polymerization activity.

Next, the olefin polymerization catalyst according to the present invention will be described.

The olefin polymerization catalyst according to the present invention is characterized by containing (A) the solid catalyst component for olefin polymerization according to the present invention, (B) an organoaluminum compound represented by the following general formula (IV);

$$R^{15}_p AlQ_{3-p} \quad (IV)$$

wherein $R^{15}$ represents an alkyl group having 1 to 4 carbon atoms, Q represents a hydrogen atom or halogen atom, and p is a real number satisfying $0<p\leq3$, provided that, when a plurality of $R^{15}$ are present, each $R^{15}$ may be identical or different from one another and when a plurality of Q are present, each Q may be identical or different from one another, and (C) an external electron-donating compound.

The olefin polymerization catalyst according to the present invention contains (B) an aluminum compound represented by the following general formula (IV);

$$R^{15}_p AlQ_{3-p} \quad (IV)$$

wherein $R^{15}$ represents an alkyl group having 1 to 4 carbon atoms, Q represents a hydrogen atom or halogen atom, and p is a real number satisfying $0<p\leq3$, provided that, when a plurality of $R^{15}$ are present, each $R^{15}$ may be identical or different from one another and when a plurality of Q are present, each Q may be identical or different from one another.

In the organoaluminum compound represented by the general formula (IV), which is not particularly limited, $R^{15}$ may be one or more selected from an ethyl group and an isobutyl group, Q may be one or more selected from a hydrogen atom, a chlorine atom, and a bromine atom, and p is preferably 2, 2.5, or 3, particularly preferably 3.

Specific examples of such organoaluminum compounds can include one or more selected from trialkylaluminums such as triethylaluminium, triisopropylaluminum, tri-n-butylaluminum, and triisobutylaluminum, halogenated alkylaluminums such as diethylaluminum chloride and diethylaluminum bromide, and diethylaluminum hydride. Among these, one or more selected from halogenated alkylaluminums such as diethylaluminum chloride or trialkylaluminums such as triethylaluminum, tri-n-butyl aluminum, and triisobutylaluminum are preferable, and one or more selected from triethylaluminum and triisobutylaluminum are more preferable.

In the olefin polymerization catalyst according to the present invention, as the external electron-donating compound (C), ones containing an oxygen atom or nitrogen atom are preferable among known external electron-donating compounds.

In the olefin polymerization catalyst according to the present invention, examples of the external electron-donating compound (C) can include one or more selected from organosilicon compounds represented by the following general formula (V);

$$R^{16}{}_q Si(OR^{17})_{4-q} \quad (V)$$

wherein $R^{16}$ represents an alkyl group having 1 to 12 carbon atoms, a vinyl group, an alkenyl group having 3 to 12 carbon atoms, a cycloalkyl group having 3 to 12 carbon atoms, a cycloalkenyl group having 3 to 12 carbon atoms, an aromatic hydrocarbon group having 6 to 15 carbon atoms, or an aromatic hydrocarbon group having 6 to 15 carbon atoms and having a substituent, provided that, when a plurality of $R^{16}$ are present, the plurality of $R^{16}$ may be identical or different from one another, $R^{17}$ represents an alkyl group having 1 to 4 carbon atoms, a vinyl group, an alkenyl group having 3 to 12 carbon atoms, a cycloalkyl group having 3 to 6 carbon atoms, an aromatic hydrocarbon group having 6 to 12 carbon atoms, or an aromatic hydrocarbon group having 7 to 12 carbon atoms and having a substituent, provided that, when a plurality of $R^{17}$ are present, the plurality of $R^{17}$ may be identical or different from one another, and q is an integer satisfying $0 \leq q \leq 3$, and aminosilane compounds represented by the general formula (VI);

$$(R^{18}R^{19}N)_s SiR^{20}{}_{4-s} \quad (VI)$$

wherein $R^{18}$ and $R^{19}$ each represent a hydrogen atom, an alkyl group having 1 to 20 carbon atoms, a vinyl group, an alkenyl group having 3 to 20 carbon atoms, cycloalkyl group having 3 to 20 carbon atoms, a cycloalkenyl group having 3 to 20 carbon atoms, or an aryl group having 6 to 20 carbon atoms, Rn and $R^{19}$ may be identical or different from each other or may bond with each other to form a ring, and when a plurality of $R^{18}R^{19}N$ groups are present, the plurality of $R^{18}R^{19}N$ groups may be identical or different from one another, $R^{20}$ represents an alkyl group having 1 to 20 carbon atoms, a vinyl group, an alkenyl group having 3 to 12 carbon atoms, an alkoxy group having 1 to 20 carbon atoms, a vinyloxy group, an alkenyloxy group having 3 to 20 carbon atoms, a cycloalkyl group having 3 to 20 carbon atoms, a cycloalkyloxy group having 3 to 20 carbon atoms, an aryl group having 6 to 20 carbon atoms, or an aryloxy group having 6 to 20 carbon atoms, provided that, when a plurality of $R^{20}$ are present, the plurality of $R^{20}$ may be identical or different from one another, and s is an integer of 1 to 3.

Examples of the organosilicon compound represented by the general formula (V) or the aminosilane compound represented by the general formula (VI) can include phenylalkoxysilanes, alkylalkoxysilanes, phenylalkylalkoxysilanes, cycloalkylalkoxysilanes, alkyl(cycloalkyl)alkoxysilanes, (alkylamino)alkoxysilanes, alkyl(alkylamino)alkoxysilanes, cycloalkyl(alkylamino)alkoxysilanes, tetraalkoxysilanes, tetrakis(alkylamino)silanes, alkyltris(alkylamino)silanes, dialkylbis(alkylamino)silanes, and trialkyl(alkylamino)silanes.

Specific examples of the organosilicon compound represented by the general formula (V) or the aminosilane compound represented by the general formula (VI) can include one or more selected from n-propyltriethoxysilane, cyclopentyltriethoxysilane, phenyltrimethoxysilane, phenyltriethoxysilane, t-butyltrimethoxysilane, diisopropyldimethoxysilane, isopropylisobutyldimethoxysilane, diisopentyldimethoxysilane, bis(2-ethylhexyl)dimethoxysilane, t-butylmethyldimethoxysilane, t-butylethyldimethoxysilane, dicyclopentyldimethoxysilane, dicyclohexyldimethoxysilane, cyclohexylcyclopentyldimethoxysilane, cyclohexylmethyldimethoxysilane, tetraethoxysilane, tetrabutoxysilane, bis(ethylamino)methylethylsilane, bis(ethylamino)t-butylmethylsilane, bis(ethylamino)dicyclohexylsilane, dicyclopentylbis(ethylamino)silane, bis(methylamino)(methylcyclopentylamino)methylsilane, diethylaminotriethoxysilane, bis(cyclohexylamino)dimethoxysilane, bis(perhydroisoquinolino)dimethoxysilane, bis(perhydroquinolino)dimethoxysilane, and ethyl(isoquinolino)dimethoxysilane. Among these, one or more selected from n-propyltriethoxysilane, phenyltrimethoxysilane, t-butylmethyldimethoxysilane, t-butylethyldimethoxysilane, diisopropyldimethoxysilane, isopropylisobutyldimethoxysilane, diisopentyldimethoxysilane, diphenyldimethoxysilane, dicyclopentyldimethoxysilane, cyclohexylmethyldimethoxysilane, tetramethoxysilane, tetraethoxysilane, t-butylmethylbis(ethylamino)silane, bis(ethylamino)dicyclohexylsilane, dicyclopentylbis(ethylamino)silane, bis(perhydroisoquinolino)dimethoxysilane, and diethylaminotriethoxysilane are preferable.

In the olefin polymerization catalyst according to the present invention, the content ratio of (A) the solid catalyst component for olefin polymerization, (B) the organoaluminum compound represented by the general formula (IV), and (C) the external electron-donating compound, which can be optionally selected as long as the effect of the present invention can be achieved, is not particularly limited. (B) The organoaluminum compound represented by the general formula (IV) is used in an amount of preferably 1 to 2000 mol, preferably 50 to 1000 mol, per mol of the titanium atoms in the solid catalyst component for olefin polymerization (A). (C) The external electron-donating compound is used in an amount of preferably 0.002 to 10 mol, more preferably 0.01 to 2 mol, still more preferably 0.01 to 0.5 mol, per mol of (B) the organoaluminum compound represented by the general formula (IV).

The method for producing the olefin polymerization catalyst according to the present invention is not particularly limited, and the catalyst can be produced by contacting (A) the solid catalyst component for olefin polymerization, (B) the organoaluminum compound represented by the general formula (IV), and (C) the external electron-donating compound with one another by a known method.

The components described above may be contacted with one another in any order, and examples of the contact order are as follows:

(i) (A) the solid catalyst component for olefin polymerization→(C) the external electron-donating compound→(B) the organoaluminum compound represented by the general formula (IV)

(ii) (B) the organoaluminum compound represented by the general formula (IV)→(C) the external electron-donating compound→(A) the solid catalyst component for olefin polymerization obtained by the production method of the present invention (iii) (C) the external electron-donating compound→(A) the solid catalyst component for olefin polymerization→(B) the organoaluminum compound represented by the general formula (IV)

(iv) (C) the external electron-donating compound→(B) the organoaluminum compound represented by the general formula (IV)→(A) the solid catalyst component for olefin polymerization In the contact examples (i) to (iv), the contact example (ii) is preferable.

It should be noted that, in the contact examples (i) to (iv), "→" means a contact order. For example, "(A) the solid catalyst component for olefin polymerization→(B) the organoaluminum compound represented by the general formula (IV)→(C) the external electron-donating compound" means that the organoaluminum compound represented by the general formula (IV) is added to (A) the solid catalyst component for olefin polymerization to contact (A) and (B) with each other and then, (C) the external electron-donating compound is added to the mixture to contact (C) and these with each other.

The olefin polymerization catalyst according to the present invention may be prepared by contacting (A) the solid catalyst component for olefin polymerization, (B) the organoaluminum compound represented by the general formula (IV), and (C) the external electron-donating compound with one another in the absence of an olefin or in the presence of an olefin (in a polymerization system).

According to the present invention, it is possible to provide an olefin polymerization catalyst which may reduce the formation rate of a fine powder and form a polymer having an excellent particle size distribution under high polymerization activity.

Next, the method for producing an olefin polymer according to the present invention will be described.

The method for producing an olefin polymer according to the present invention is characterized in that an olefin is polymerized in the presence of the olefin polymerization catalyst according to the present invention.

In the method for producing an olefin polymer according to the present invention, an olefin may be homopolymerized or copolymerized.

In the method for producing an olefin polymer according to the present invention, examples of the olefin can include one or more selected from ethylene, propylene, 1-butene, 1-pentene, 4-methyl-1-pentene, and vinylcyclohexane. Ethylene, propylene, or 1-betene is preferable, and propylene is more preferable.

When propylene is polymerized, polypropylene may be copolymerized with another olefin. Block copolymerization of propylene with another α-olefin is preferable. A block copolymer obtained by block copolymerization is a polymer that includes segments in which the composition of two or more monomers changes consecutively. Such a block copolymer is a polymer in which two or more polymer chains (segments) that differ in polymer primary structure, such as type of monomer, type of comonomer, comonomer composition, comonomer content, comonomer sequence, and stereoregularity, are linked within one molecular chain.

The olefin to be copolymerized is preferably α-olefins having 2 to 20 carbon atoms (except for propylene having 3 carbon atoms), and specific examples thereof include ethylene, 1-butene, 1-pentene, 4-methyl-1-pentene, and vinylcyclohexane. One or more of these olefins may be used in combination. Especially, ethylene and 1-butene are preferably used.

In the method for producing an olefin polymer of the present invention, the olefin may be polymerized in the presence or absence of an organic solvent.

The olefin to be polymerized may be used either in a gaseous state or a liquid state.

The olefin can be polymerized in, for example, a reactor such as an autoclave in the presence of the olefin polymerization catalyst according to the present invention while heated under pressure.

In the method for producing an olefin polymer according to the present invention, the polymerization temperature is normally 200° C. or less, preferably 100° C. or less. The polymerization temperature is preferably 60 to 100° C., more preferably 70 to 90° C. from the viewpoint of improving the activity and stereoregularity. In the method for producing an olefin polymer of the present invention, the polymerization pressure is preferably 10 MPa or less, more preferably 5 MPa or less.

Either a continuous polymerization method or a batch polymerization method may be used. The polymerization reaction may be carried out in a single stage or in two or more stages.

In the method for producing an olefin polymer of the present invention, when the olefin is polymerized (hereinafter may be appropriately referred to as "main polymerization"), preliminary polymerization may be effected by contacting a portion or all of the components of the olefin polymerization catalyst according to the present invention with the olefin.

When the preliminary polymerization is effected, the components of the olefin polymerization catalyst according to the present invention may be contacted with the olefin in any order. It is preferable that an organoaluminum compound be first loaded to a preliminary polymerization system containing an inert gas atmosphere or an olefin gas atmosphere, the solid catalyst component for olefin polymerization according to the present invention be contacted with the compound, and then, one or more olefins such as propylene be contacted with the mixture. Alternatively, it is preferable that an organoaluminum compound be first loaded to a preliminary polymerization system containing an inert gas atmosphere or an olefin gas atmosphere, an external electron-donating compound be contacted with the compound, the solid catalyst component for olefin polymerization of the present invention be further contacted with the mixture, and then, one or more olefins such as propylene be contacted with the mixture. Olefins similar to those in main polymerization or monomers such as styrene may be used for the preliminary polymerization. The preliminary polymerization conditions may be the same as the above polymerization conditions.

Effecting the preliminary polymerization improves the catalytic activity and easily improves the stereoregularity, the particle properties, and the like of the resulting polymer.

According to the present invention, it is possible to provide a method for producing an olefin polymer which may reduce the formation rate of a fine powder and form a polymer having an excellent particle size distribution under high polymerization activity.

Particularly, according to the present invention, it is possible to produce a polymer powder containing an extremely reduced amount of a fine powder and having a good particle shape and a narrow particle size distribution at a high yield, to improve the handling operability of the polymer powder formed at the time of polymerization operation, and to suitably suppress occurrence of clogging or the like caused by a fine powder contained in the polymer powder formed.

The method for producing an olefin polymer according to the present invention can be applied to polyolefin production processes particularly by the vapor phase method.

EXAMPLES

The present invention now will be described further specifically with reference to Examples and Comparative Examples, but the invention should not be limited to these Examples in any way.

In the Examples and Comparative Examples shown below, the content of titanium atoms in the solid catalyst component for olefin polymerization, the average particle diameter of the alkoxymagnesium, and the average particle diameter and the amount of a fine powder of 5 μm or less of the solid catalyst component are measured in accordance to the following methods.

(Titanium Atom Content in Solid Catalyst Component for Olefin Polymerization)

The titanium atom content in the solid catalyst component for olefin polymerization was measured in accordance with the method (oxidation-reduction titration) specified in JIS8311-1997 "Method for determination of titanium in titanium ores".

(Method for Measuring Average Particle Diameter, Particle Size Distribution Index (SPAN), and Amount of Fine Powder of 5 μm or less of Alkoxymagnesium (Secondary Particles))

The particle diameter corresponding to the 90% volumetric cumulative particle size ($D_{90}$), average particle diameter (particle diameter corresponding to the 50% volumetric cumulative particle size), and particle diameter corresponding to the 10% volumetric cumulative particle size ($D_{10}$) of the alkoxymagnesium (secondary particles) and the amount of a fine powder of 5 μm or less of the alkoxymagnesium were measured using a laser-diffraction particle size distribution analyzer that supports dry dispersion (Mastersizer 3000 manufactured by Malvern Panalytical Ltd.) by the laser diffraction method in a dry state under the following measurement conditions by automatically measuring the volumetric cumulative particle size distribution of particles to be measured.

(Measuring Conditions)

Measurement range: 0.01 μm to 3500 μm
Dispersion form: dry state
Dispersion pressure: 1.5 bar (alkoxymagnesium)
0.4 bar (solid catalyst component)
Laser scattered light intensity: 0.3 to 5.0%

$D_{90}$, the average particle diameter, and $D_{10}$ of the alkoxymagnesium (secondary particles) obtained by the above measurement were used to determine the particle size distribution index (SPAN) by the following expression.

Particle size distribution index (SPAN)=(particle diameter corresponding to the 90% volumetric cumulative particle size ($D_{90}$)–particle diameter corresponding to the 10% volumetric cumulative particle size ($D_{10}$))/average particle diameter (particle diameter corresponding to the 50% volumetric cumulative particle size)

During production of the alkoxymagnesium, the average particle diameter and the amount of a fine powder of 5 μm or less of a solid obtained before contact with the carboxylic acid ester were measured in the same manner as the method for measuring the average particle diameter and the amount of a fine powder of 5 μM or less of the alkoxymagnesium aforementioned.

(Method for Measuring Average Particle Diameter of Primary Particles Constituting Alkoxymagnesium)

The alkoxymagnesium was photographed on a scanning electron microscope (JSM-7500F manufactured by JEOL Ltd.) at an accelerating voltage of 5 KV and a magnification of 30,000. After photographing, the negative image was visually analyzed, and the average particle diameter of the primary particles constituting the alkoxymagnesium (particle diameter corresponding to the 50% volumetric cumulative particle size) was calculated from the longest diameter of 100 or more particles by a statistical analysis approach.

Example 1

1. Preparation of Diethoxymagnesium (1) Solid Formation Step

To a 2000 ml round-bottom flask sufficiently purged with nitrogen gas and equipped with a stirrer and a reflux condenser, 5 g of metal magnesium fine powder having a particle diameter of 100 mesh or less, 125 ml of ethanol at room temperature, and 3 g of iodine were loaded to form a suspension.

Then, the temperature of the suspension was raised under stirring, and the reaction was started under reflux of ethanol. After the reaction was started, an operation of simultaneously adding 5 g of metal magnesium powder having a particle diameter 100 mesh or less and 62 ml of ethanol into the flask was carried out four times over 20 minutes. After addition was finished, the mixture was maintained under reflux of ethanol and under stirring for 10 hours (the total amount of magnesium added was 25 g, the total amount of ethanol added was 373 ml (about 294.3 g), and metal magnesium/ethanol totally added=1/11.8). Then, after the mixture was cooled to room temperature, the supernatant was decanted. The residue was vacuum dried to obtain about 100 g of a solid. The resulting solid had an average particle diameter of 58.3 μm and a content of a fine powder of 5 μm or less of 5.1% by mass.

(2) Step of Contacting with Carboxylic Acid Ester

To a 500 ml round-bottom flask sufficiently purged with nitrogen gas and equipped with a stirrer, 20 g of the solid obtained the above (1), 115 ml of toluene at ordinary temperature, and 30 mmol of bis(2-ethylhexyl)maleate were placed and stirred to form a suspension.

The temperature of the suspension was raised to 60° C. under stirring to contact the components of the suspension with one another at 60° C. for an hour. Then, the suspension obtained was left to stand, and the supernatant was removed by decantation (removal step). Additionally, a washing step of adding 80 ml of toluene at 60° C. and stirring the mixture was repeated three times to obtain a diethoxymagnesium.

The diethoxymagnesium obtained also had an average particle diameter of secondary particles D2 of 57.8 μm, a particle size distribution index (SPAN) of 0.8, an average particle diameter of the primary particles constituting the secondary particles D1 of 0.6 μm, a ratio represented by the average particle diameter of the primary particles D1/the average particle diameter of the secondary particles D2 of 0.01, a content of a fine powder of 5 μm or less of 0% by mass, a specific surface area of 14 m$^2$/g, and a bulk density of 0.32 g/ml.

After the diethoxymagnesium was sufficiently washed with heptane, the solid and liquid were separated. The content of maleic acid diester in the diethoxymagnesium measured 0% by mass. The diethoxymagnesium formed no adduct of bis(2-ethylhexyl)maleate.

The measurement results for the pore volume of pores having a pore diameter of 1 μm or less and pore volume of pores having a pore diameter of 0.1 to 0.5 μm of the diethoxymagnesium are shown in Table 1. No pore having a pore diameter more than 1 μm was measured in the diethoxymagnesium.

The result obtained by photographing the diethoxymagnesium with a scanning electron microscope (JSM-7500F manufactured by JEOL Ltd.) is shown in FIG. 1.

As shown in FIG. 1, it can be seen that the diethoxymagnesium obtained is composed of secondary particles each of which is an aggregate of primary particles, has smooth surface, and scarcely contains fine powder particles.

The supernatant removed in the removal step was further subjected to solid-liquid separation in a centrifuge, and the solid and the liquid were each dried under reduced pressure. Then, 0.3 g of diethoxymagnesium particulates liberated in the supernatant and 0.04 g of solubilized diethoxymagnesium were recovered.

2. Preparation of Solid Catalyst Component

To a 500 ml round-bottom flask sufficiently purged with nitrogen gas and equipped with a stirrer, 20 g of the diethoxymagnesium obtained in the above 1 was placed, and 160 ml of toluene, 10 ml of dimethyl diisobutylmalonate, and 40 ml of titanium tetrachloride were added thereto to form a turbid solution.

Thereafter, the temperature of the turbid solution was raised and the solution was reacted under stirring at 110° C. for three hours. After the reaction was finished, the solid product obtained was washed with 100 ml of toluene at 90° C. four times. Newly added were 40 ml of titanium tetrachloride and 60 ml of toluene thereto. The temperature of the mixture was raised to 100° C., and the mixture was reacted under stirring for two hours.

After the reaction was finished, the mixture was washed with 100 ml of n-heptane at 40° C. seven times to obtain an intended solid catalyst component.

The solid catalyst component obtained had a titanium content ratio of 2.6% by mass, an internal electron-donating compound content ratio of 13.0% by mass (13.0% by mass of diisobutylmalonic acid diester and 0.0% by mass of maleic acid diester), an average particle diameter $D_{50}$ of 47.1 μm, and an amount of a fine powder of 5 μm or less of 0% by mass.

The average particle diameter and the amount of a fine powder of 5 μm or less of the solid catalyst component were measured in the same manner as for the average particle diameter and the amount of a fine powder of 5 μm or less of the alkoxymagnesium (secondary particles).

3. Formation of Olefin Polymerization Catalyst and Polymerization

To an autoclave equipped with a stirred and having an internal volume of 2.0 liters and completely purged with nitrogen gas, 1.32 mmol of triethylaluminum, 0.13 mmol of diisopropyldimethoxysilane (DIPDMS), and 0.0026 mmol of (A) the solid catalyst component in terms of titanium atoms were loaded to form an olefin polymerization catalyst.

Thereafter, 1.5 liters of hydrogen gas and 1.4 liters of liquefied propylene were loaded thereto. After preliminary polymerization at 20° C. for 5 minutes, the temperature was raised, and the mixture was subjected to polymerization reaction at 70° C. for an hour.

The polymerization activity, melt flow rate (MFR, g-PP/10 minutes), amount of a fine powder of 75 μm or less, average particle diameter ($D_{50}$), particle size distribution index (SPAN), and bulk density (BD) of the polymer obtained were measured by the following methods. The results are listed in Table 2.

<Polymerization Activity>

The polymerization activity (kg-PP/g-cat), which indicates an amount of the polymer formed (F) kg per gram of the solid catalyst component and per hour of the polymerization time was calculated by the following expression.

Polymerization activity (kg-PP/g-cat)=polymer formed (F) kg/solid catalyst component g/hour <Method for Measuring Average Particle Diameter $D_{50}$, Fine Powder of 75 μm or Less, and Particle Size Distribution Index (SPAN) of Polymer>

With respect to the amount of the fine powder of 75 μm or less of the polymer obtained, the volumetric cumulative particle size distribution of the polymer was automatically measured using a digital image analysis-type particle diameter distribution analyzer ("CAMSIZER" manufactured by HORIBA, Ltd.) under the following measurement conditions to obtain measurements of the average particle diameter (particle diameter corresponding to the 50% volumetric cumulative particle size ($D_{50}$)) and amount of the fine powder of a particle diameter of 75 μm or less (% by mass).

(Measuring Conditions)

Funnel position: 6 mm

Cover area of camera: basic camera: less than 3%, zoom camera: less than 10%

Target cover area: 0.5%

Width of feeder: 40 mm

Feeder control level: 57, 40 seconds

Measurement start level: 47

Maximum control level: 80

Control standard: 20

Image rate: 50% (1:2)

Definition of particle diameter: minimum Martin's diameter when the diameter of each particle was measured n times SPHT (sphericity) fitting: 1

Class upper limit: 50 points were selected within a range from 32 μm to 4,000 μm (logarithmic scale)

In accordance with the method described above, the values of the particle diameter corresponding to the 90% volumetric cumulative particle size ($D_{90}$) and particle diameter corresponding to the 10% volumetric cumulative particle size ($D_{10}$) of the polymer obtained were also simultaneously measured, and the particle size distribution index (SPAN) was calculated.

Particle size distribution index (SPAN)=$(D_{90}-D_{10})/D_{50}$

<Method for Measuring Bulk Density of Polymer (BD)>

The bulk density of the polymer was measured in accordance with JIS K6721.

Example 2

Preparation of the diethoxymagnesium, preparation of the solid catalyst component, formation of the polymerization catalyst, and polymerization were carried out under the same conditions as in Example 1 except that, in "2. Preparation of Solid Catalyst Component", dimethyl diisobutylmalonate was replaced by diethyl diisobutylmalonate in an equal molar amount. The properties of the alkoxymagnesium (diethoxymagnesium) obtained, the properties of the solid catalyst component, the properties (polymerization activity) of the catalyst, and the properties of the polymer were measured in the same manner as in Example 1.

The solid catalyst component obtained had a titanium content in the solid catalyst component of 3.2% by mass, an internal electron-donating compound content ratio of 14.0% by mass (14.0% by mass of diisobutylmalonic acid diester and 0.0% by mass of maleic acid diester), an average particle diameter $D_{50}$ of 46.3 μm, and an amount of a fine powder of 5 μm or less of 0.2% by mass. The results are shown in Table 1 and Table 2.

Example 3

Preparation of the diethoxymagnesium, preparation of the solid catalyst component, formation of the polymerization catalyst, and polymerization were carried out under the same conditions as in Example 1 except, that in "2. Preparation of Solid Catalyst Component", dimethyl diisobutylmalonate was replaced by 2-isopropyl-2-isopentyl-1,3-dimethoxypropane in an equal molar amount. The properties of the alkoxymagnesium (diethoxymagnesium) obtained, the properties of the solid catalyst component, the properties (polymerization activity) of the catalyst, and the properties of the polymer were measured in the same manner as in Example 1.

The solid catalyst component obtained had a titanium content in the solid catalyst component of 2.0% by mass, an average particle diameter $D_{53}$ of 50.6 μm, and an amount of a fine powder of 5 μm or less of 0.4% by mass. The results are shown in Table 1 and Table 2.

Example 4

Preparation of the diethoxymagnesium, preparation of the solid catalyst component, formation of the polymerization catalyst, and polymerization were carried out under the same conditions as in Example 1 except that, in "2. Preparation of Solid Catalyst Component", dimethyl diisobutylmalonate was replaced by dibutyl phthalate in an equal molar amount. The properties of the alkoxymagnesium (diethoxymagnesium) obtained, the properties of the solid catalyst component, the properties (polymerization activity) of the catalyst, and the properties of the polymer were measured in the same manner as in Example 1.

The solid catalyst component obtained had a titanium content in the solid catalyst component of 2.8% by mass, an average particle diameter $D_{53}$ of 48.5 μm, and an amount of a fine powder of 5 μm or less of 0.6% by mass. The results are shown in Table 1 and Table 2.

Example 5

1. Preparation of Diethoxymagnesium

The diethoxymagnesium was prepared in the same manner as in Example 1 "1. Preparation of Diethoxymagnesium".

2. Preparation of Solid Catalyst Component

To a 500 ml round-bottom flask sufficiently purged with nitrogen gas and equipped with a stirrer, 20 g of the diethoxymagnesium obtained in the above 1 was placed, and 160 ml of toluene, 10 ml of dimethyl diisobutylmalonate, and 40 ml of titanium tetrachloride were added thereto to form a turbid solution. Thereafter, the temperature of the mixed solution was raised and the solution was reacted under stirring at 110° C. for three hours. After the reaction was finished, the solid product obtained was washed with 100 ml of toluene at 90° C. four times. To the product, 40 ml of titanium tetrachloride, 1 ml of diethyl maleate, and 60 ml of toluene were newly added. The temperature of the mixture was raised to 100° C., and the mixture was reacted under stirring for two hours. After the reaction was finished, the mixture was washed with 100 ml of n-heptane at 40° C. seven times to obtain a solid catalyst component.

When the properties of the solid catalyst component obtained was measured in the same manner as in Example 1, the titanium content was 2.1% by mass, the internal electron-donating compound content ratio was 14.5% by mass (10.5% by mass of diisobutylmalonic acid diester and 4.0% by mass of maleic acid diester), the average particle diameter $D_{50}$ was 49.2 μm, and the amount of a fine powder of 5 μm or less was 0% by mass.

3. Formation of Polymerization Catalyst and Polymerization

Polymerization was carried out in the same manner as in Example 1 except that the solid catalyst component obtained in the above 2, and the properties of the catalyst obtained (polymerization activity) and the properties of the polymer were measured in the same manner as in Example 1

The results are shown in Table 1 and Table 2.

Example 6

Preparation of the diethoxymagnesium, preparation of the solid catalyst component, formation of the polymerization catalyst, and polymerization were carried out under the same conditions as in Example 1 except that, in "1. Preparation of Diethoxymagnesium", bis(2-ethylhexyl)maleate was replaced by diethyl maleate in an equal molar amount. The properties of the alkoxymagnesium (diethoxymagnesium) obtained, the properties of the solid catalyst component, the properties (polymerization activity) of the catalyst, and the properties of the polymer were measured in the same manner as in Example 1.

The diethoxymagnesium obtained were composed of secondary particles each of which was an aggregate of primary particles, had smooth surface, and scarcely contained fine powder particles. The diethoxymagnesium obtained also had an average particle diameter of secondary particles D2 of 56.8 μm, an SPAN of 0.8, an average particle diameter of the primary particles constituting the secondary particles D1 of 0.7 μm, a ratio represented by the average particle diameter of the primary particles/the average particle diameter of the secondary particles of 0.01, a content of a fine powder of 5 μm or less of 1.5% by mass, a specific surface area of 15 m$^2$/g, and a bulk density of 0.31 g/ml. The measurement results for the pore volume of pores having a pore diameter of 1 μm or less and pore volume of pores having a pore diameter of 0.1 to 0.5 μm of the diethoxymagnesium obtained are shown in Table 1. No pore having a pore diameter more than 1 μm was measured in the diethoxymagnesium.

The supernatant removed in the removal step was further subjected to solid-liquid separation in a centrifuge, and the solid and the liquid were each dried under reduced pressure. Then, 0.2 g of a solid component derived from diethoxymagnesium particulates liberated in the supernatant and 0.03 g of solubilized diethoxymagnesium in the supernatant were recovered.

The solid catalyst component obtained from the diethoxymagnesium had a titanium content of 2.3% by mass, an internal electron-donating compound content ratio of 12.6% by mass (12.6% by mass of diisobutylmalonic acid diester and 0.0% by mass of maleic acid diester), an average particle diameter $D_{50}$ of 45.6 μm, and an amount of a fine powder of 5 μm or less of 0.5% by mass. The results are shown in Table 1 and Table 2.

Example 7

Preparation of the diethoxymagnesium, preparation of the solid catalyst component, formation of the polymerization catalyst, and polymerization were carried out under the same conditions as in Example 1 except that, in "1. Preparation of Diethoxymagnesium" of Example 1, bis(2-ethylhexyl)maleate was replaced by dimethyl diisobuthylmalonate in an equal molar amount. The properties of the alkoxymagnesium (diethoxymagnesium) obtained, the properties of the solid catalyst component, the properties (polymerization activity) of the catalyst, and the properties of the polymer were measured in the same manner as in Example 1.

The diethoxymagnesium obtained were composed of secondary particles each of which was an aggregate of primary particles, had smooth surface, and scarcely contained fine powder particles. The diethoxymagnesium obtained also had an average particle diameter of secondary particles D2 of 56.5 μm, an SPAN of 1.0, an average particle diameter of the primary particles constituting the secondary particles D1 of 0.5 μm, a ratio represented by the average particle diameter of the primary particles D1/the average particle diameter of the secondary particles of 0.01, a content of a fine powder of 5 μm or less of 1.6% by mass, a specific surface area of 15 m$^2$/g, and a bulk density of 0.32 g/ml. The measurement results for the pore volume of pores having a pore diameter of 1 μm or less and pore volume of pores having a pore diameter of 0.1 to 0.5 μm of the diethoxymagnesium obtained are shown in Table 1. No pore having a pore diameter more than 1 μm was measured in the diethoxymagnesium.

The supernatant removed in the removal step was further subjected to solid-liquid separation in a centrifuge, and the solid and the liquid were each dried under reduced pressure. Then, 0.2 g of a solid component derived from diethoxymagnesium particulates liberated in the supernatant and 0.02 g of solubilized diethoxymagnesium in the supernatant were recovered.

The solid catalyst component obtained from the diethoxymagnesium had a titanium content of 1.9% by mass, a diisobutylmalonic acid diester content ratio of 13.5% by mass, an average particle diameter D$_{50}$ of 46.1 μm, and an amount of a fine powder of 5 μm or less of 0.5% by mass. The results are shown in Table 1 and Table 2.

Example 8

Preparation of the diethoxymagnesium, preparation of the solid catalyst component, formation of the polymerization catalyst, and polymerization were carried out under the same conditions as in Example 1 except that, in "1. Preparation of Diethoxymagnesium" of Example 1, the amount of bis(2-ethylhexyl)maleate added was changed from 30 mmol to 7 mmol. The properties of the alkoxymagnesium (diethoxymagnesium) obtained, the properties of the solid catalyst component, the properties (polymerization activity) of the catalyst, and the properties of the polymer were measured in the same manner as in Example 1.

The diethoxymagnesium obtained were composed of secondary particles each of which was an aggregate of primary particles, had smooth surface, and scarcely contained fine powder particles. The diethoxymagnesium obtained also had an average particle diameter of secondary particles D2 of 56.8 μm, an SPAN of 0.8, an average particle diameter of the primary particles constituting the secondary particles D1 of 0.7 μm, a ratio represented by the average particle diameter of the primary particles D1/the average particle diameter of the secondary particles D2 of 0.01, a content of a fine powder of 5 μm or less of 1.8% by mass, a specific surface area of 19 m$^2$/g, and a bulk density of 0.31 g/ml. The measurement results for the pore volume of pores having a pore diameter of 1 μm or less and pore volume of pores having a pore diameter of 0.1 to 0.5 μm of the diethoxymagnesium obtained are shown in Table 1. No pore having a pore diameter more than 1 μm was measured in the diethoxymagnesium.

The supernatant removed in the removal step was further subjected to solid-liquid separation in a centrifuge, and the solid and the liquid were each dried under reduced pressure. Then, 0.2 g of diethoxymagnesium particulates liberated in the supernatant and 0.03 g of solubilized diethoxymagnesium were recovered.

The solid catalyst component obtained from the diethoxymagnesium had a titanium content of 2.3% by mass, an internal electron-donating compound content ratio of 12.9% by mass (the diisobutylmalonic acid diester content is 12.9% by mass, and the maleic acid diester content is 0.0% by mass), an average particle diameter D$_{50}$ of 45.6 μm, and an amount of a fine powder of 5 μm or less of 0.8% by mass. The results are shown in Table 1 and Table 2.

Example 9

Preparation of the diethoxymagnesium, preparation of the solid catalyst component, formation of the polymerization catalyst, and polymerization were carried out under the same conditions as in Example 1 except that, in "1. Preparation of Diethoxymagnesium" of Example 1, the amount of bis(2-ethylhexyl)maleate added was changed from 30 mmol to 14 mmol. The properties of the alkoxymagnesium (diethoxymagnesium) obtained, the properties of the solid catalyst component, the properties (polymerization activity) of the catalyst, and the properties of the polymer were measured in the same manner as in Example 1.

The diethoxymagnesium obtained were composed of secondary particles each of which was an aggregate of primary particles, had smooth surface, and scarcely contained fine powder particles. The diethoxymagnesium obtained also had an average particle diameter of secondary particles D2 of 57.6 μm, an SPAN of 0.9, an average particle diameter of the primary particles constituting the secondary particles D1 of 0.6 μm, a ratio represented by the average particle diameter of the primary particles D1/the average particle diameter of the secondary particles D2 of 0.01, a content of a fine powder of 5 μm or less of 0.8% by mass, a specific surface area of 16 m$^2$/g, and a bulk density of 0.31 g/ml. The measurement results for the pore volume of pores having a pore diameter of 1 μm or less and pore volume of pores having a pore diameter of 0.1 to 0.5 μm of the diethoxymagnesium obtained are shown in Table 1. No pore having a pore diameter more than 1 μm was measured in the diethoxymagnesium.

The supernatant removed in the removal step was further subjected to solid-liquid separation in a centrifuge, and the solid and the liquid were each dried under reduced pressure. Then, 0.4 g of diethoxymagnesium particulates liberated in the supernatant and 0.04 g of solubilized diethoxymagnesium were recovered.

The solid catalyst component obtained from the diethoxymagnesium had a titanium content of 2.3% by mass, an internal electron-donating compound content ratio of 13.3% by mass (13.3% by mass of diisobutylmalonic acid diester and 0% by mass of maleic acid diester), an average particle diameter D$_{50}$ of 47.4 μm, and an amount of a fine powder of 5 μm or less of 0% by mass. The results are shown in Table 1 and Table 2.

Example 10

Preparation of the diethoxymagnesium, preparation of the solid catalyst component, formation of the polymerization catalyst, and polymerization were carried out under the same conditions as in Example 1 except that, in "1. Preparation of Diethoxymagnesium" of Example 1, the amount of bis(2-ethylhexyl)maleate added was changed from 30 mmol to 60 mmol. The properties of the alkoxymagnesium (diethoxymagnesium) obtained, the properties of the solid catalyst component, the properties (polymerization activity) of the catalyst, and the properties of the polymer were measured in the same manner as in Example 1.

The diethoxymagnesium obtained were composed of secondary particles each of which was an aggregate of primary particles, had smooth surface, and scarcely contained fine powder particles. The diethoxymagnesium obtained also had an average particle diameter of secondary particles D2 of 57.8 µm, an SPAN of 0.8, an average particle diameter of the primary particles constituting the secondary particles D1 of 0.6 µm, a ratio represented by the average particle diameter of the primary particles D1/the average particle diameter of the secondary particles D2 of 0.01, a content of a fine powder of 5 µm or less of 0% by mass, a specific surface area of 12 m$^2$/g, and a bulk density of 0.33 g/ml. The measurement results for the pore volume of pores having a pore diameter of 1 µm or less and pore volume of pores having a pore diameter of 0.1 to 0.5 µm of the diethoxymagnesium obtained are shown in Table 1. No pore having a pore diameter more than 1 µm was measured in the diethoxymagnesium.

The supernatant removed in the removal step was further subjected to solid-liquid separation in a centrifuge, and the solid and the liquid were each dried under reduced pressure. Then, 0.4 g of diethoxymagnesium particulates liberated in the supernatant and 0.06 g of solubilized diethoxymagnesium were recovered.

The solid catalyst component obtained from the diethoxymagnesium had a titanium content of 2.3% by mass, an internal electron-donating compound content ratio of 13.1% by mass (13.1% by mass of diisobutylmalonic acid diester and 0% by mass of maleic acid diester), an average particle diameter D$_{50}$ of 48.9 µm, and an amount of a fine powder of 5 µm or less of 0% by mass. The results are shown in Table 1 and Table 2.

Example 11

1. Preparation of Diethoxymagnesium
(1) Solid Formation Step

To a 2000 ml round-bottom flask sufficiently purged with nitrogen gas and equipped with a stirrer and a reflux condenser, 5 g of metal magnesium fine powder having a particle diameter of 144 mesh or less, 125 ml of ethanol at room temperature, and 3 g of iodine were loaded to form a suspension.

Then, the temperature of the suspension was raised under stirring, and the reaction was started under reflux of ethanol. After the reaction was started, an operation of simultaneously adding 5 g of metal magnesium powder having a particle diameter 100 mesh or less and 62 ml of ethanol into the flask was carried out four times over 30 minutes. After addition was finished, the mixture was maintained under reflux of ethanol and under stirring for 10 hours (the total amount of magnesium added was 25 g, the total amount of ethanol added was 373 ml (about 294.3 g), and metal magnesium/ethanol totally added=1/11.8). Then, after the mixture was cooled to room temperature, the supernatant was decanted. The residue was vacuum dried to obtain about 100 g of a solid. The resulting solid had an average particle diameter of 20.5 µm and a content of a fine powder of 5 µm or less of 5.9% by mass.

(2) Step of Contacting with Carboxylic Acid Ester

To a 500 ml round-bottom flask sufficiently purged with nitrogen gas and equipped with a stirrer, 20 g of the solid obtained in the above (1) and 115 ml of toluene at ordinary temperature were placed and stirred and then, 30 mmol of bis(2-ethylhexyl)maleate were placed thereto and stirred.

Thereafter, the components were contacted with one another under stirring at 60° C. for an hour to obtain a suspension. Then, the suspension obtained was left to stand, and the supernatant was removed by decantation (removal step). Additionally, a washing step of adding 80 ml of toluene at 60° C. and stirring the mixture was repeated three times to obtain diethoxymagnesium. The properties of the alkoxymagnesium (diethoxymagnesium) were measured in the same manner as in Example 1.

The diethoxymagnesium obtained were composed of secondary particles each of which was an aggregate of primary particles, had smooth surface, and scarcely contained fine powder particles. The diethoxymagnesium obtained also had an average particle diameter of secondary particles D2 of 19.3 µm, a SPAN of 0.8, an average particle diameter of the primary particles constituting the secondary particles D1 of 0.6 µm, a ratio represented by the average particle diameter of the primary particles D1/the average particle diameter of the secondary particles D2 of 0.03, an amount of a fine powder of 5 µm or less of 1.6% by mass, a specific surface area of 22 m$^2$/g, and a bulk density of 0.24 g/ml.

After this diethoxymagnesium was sufficiently washed with heptane, the solid and liquid were separated. The content of maleic acid diester in the diethoxymagnesium measured 0% by mass, and the diethoxymagnesium obtained formed no adduct of maleic acid diester.

The measurement results for the pore volume of pores having a pore diameter of 1 µm or less and pore volume of pores having a pore diameter of 0.1 to 0.5 µm of the diethoxymagnesium obtained are shown in Table 1. No pore having a pore diameter more than 1 µm was measured in the diethoxymagnesium.

The supernatant removed in the removal step was further subjected to solid-liquid separation in a centrifuge, and the solid and the liquid were each dried under reduced pressure. Then, 0.5 g of diethoxymagnesium particulates liberated in the supernatant and 0.06 g of solubilized diethoxymagnesium were recovered.

2. Preparation of Solid Catalyst Component

A solid catalyst component was prepared under the same conditions as in Example 1 except that the diethoxymagnesium was used, and the properties of the solid catalyst component obtained were measured in the same manner as in Example 1.

The solid catalyst component obtained had a titanium content ratio of 3.3% by mass, an internal electron-donating compound content ratio of 12.6% by mass (12.6% by mass of diisobutylmalonic acid diester and maleic acid diester of 0% by mass), an average particle diameter D$_{50}$ of 19.2 µm, and an amount of a fine powder of 5 µm or less of 0.1% by mass.

3. Formation of Olefin Polymerization Catalyst and Polymerization

Formation of an olefin polymerization catalyst and polymerization were carried out under the same conditions as in Example 1, and the properties of the catalyst obtained (polymerization activity) and the properties of the polymer were measured in the same manner as in Example 1.

The results are shown in Table 1 and Table 2.

Comparative Example 1

Preparation of the diethoxymagnesium, preparation of the solid catalyst component, formation of the polymerization catalyst, and polymerization were carried out under the same conditions as in Example 1 except that in, "1. Preparation of Diethoxymagnesium" of Example 1, bis(2-ethylhexyl) maleate was not added. The properties of the alkoxymagnesium (diethoxymagnesium) obtained, the properties of the solid catalyst component, the properties (polymerization activity) of the catalyst, and the properties of the polymer were measured in the same manner as in Example 1.

The diethoxymagnesium obtained also had an average particle diameter of secondary particles D2 of 52.9 µm, an SPAN of 1.1, an average particle diameter of the primary particles constituting the secondary particles D1 of 0.7 µm, a ratio represented by the average particle diameter of the primary particles D1/the average particle diameter of the secondary particles D2 of 0.01, a content of a fine powder of 5 µm or less of 4.1% by mass, a specific surface area of 25 m$^2$/g, and a bulk density of 0.30 g/ml. The measurement results for the pore volume of pores having a pore diameter of 1 µm or less and pore volume of pores having a pore diameter of 0.1 to 0.5 µm of the diethoxymagnesium obtained are shown in Table 1. No pore having a pore diameter more than 1 µm was measured in the diethoxymagnesium.

The solid catalyst component obtained from the diethoxymagnesium had a titanium content of 3.2% by mass, a content of diisobutylmalonic acid diester of 14.5% by mass, an average particle diameter D$_{50}$ of 52.9 µm, and an amount of a fine powder of 5 µm or less of 4.1% by mass. The results are shown in Table 1 and Table 2.

Figure 2:
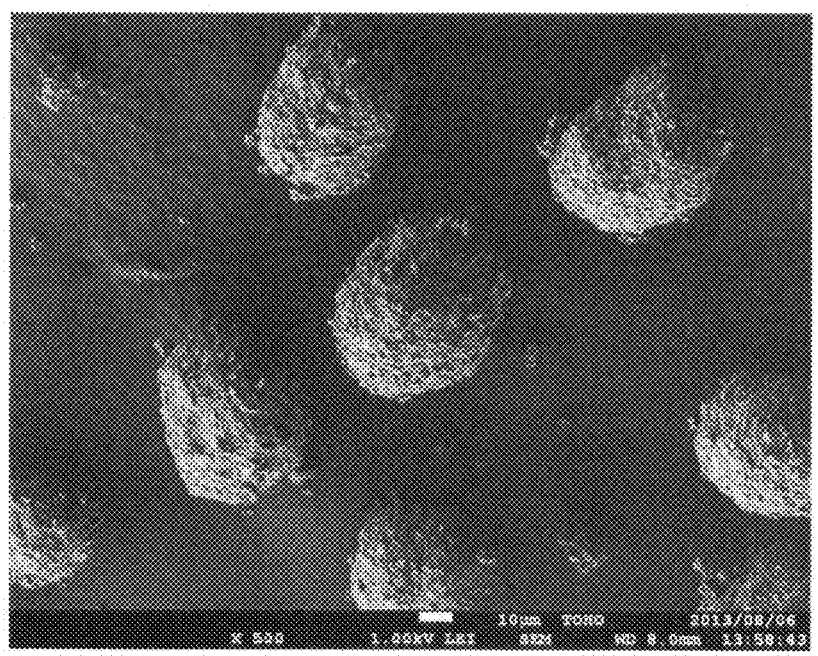
FIG. 2 shows the appearance shape of an alkoxymagnesium obtained in a Comparative Example of the present invention.

The result obtained by photographing the diethoxymagnesium obtained by the method aforementioned using a scanning electron microscope (JSM-7500F manufactured by JEOL Ltd.) is shown in FIG. 2.

The diethoxymagnesium obtained contains a large number of fine-powder particles, the surface of which much unevenness has been formed.

Comparative Example 2

Preparation of the diethoxymagnesium, preparation of the solid catalyst component, formation of the polymerization catalyst, and polymerization were carried out under the same conditions as in Example 1 except that, in "1. Preparation of Diethoxymagnesium" of Example 1, bis(2-ethylhexyl) maleate was replaced by 9,9-bis(methoxymethyl)fluorene in an equal molar amount. The properties of the alkoxymagnesium (diethoxymagnesium) obtained, the properties of the solid catalyst component, the properties (polymerization activity) of the catalyst, and the properties of the polymer were measured in the same manner as in Example 1.

The diethoxymagnesium obtained also had an average particle diameter of secondary particles D2 of 57.6 µm, an SPAN of 1.2, an average particle diameter of the primary particles constituting the secondary particles D1 of 0.7 µm, a ratio represented by the average particle diameter of the primary particles D1/the average particle diameter of the secondary particles D2 of 0.01, a content of a fine powder of 5 mm or less of 3.4% by mass, a specific surface area of 15 m$^2$/g, and a bulk density of 0.33 g/ml. The measurement results for the pore volume of pores having a pore diameter of 1 µm or less and pore volume of pores having a pore diameter of 0.1 to 0.5 µm of the diethoxymagnesium obtained are shown in Table 1. No pore having a pore diameter more than 1 µm was measured in the diethoxymagnesium.

The solid catalyst component obtained had a titanium content of 3.0% by mass, an internal electron-donating compound content ratio of 12.8% by mass (12.8% by mass of diisobutylmalonic acid diester and 0.0% by mass of 9,9-bis(methoxymethyl)fluorene, an average particle diameter D$_{50}$ of 47.2 µm, and an amount of a fine powder of 5 µm or less of 3.5% by mass. The results are shown in Table 1 and Table 2.

TABLE 1

| | Carboxylic acid ester | | Physical properties of diethoxy magnesium | | | | | | | | |
|---|---|---|---|---|---|---|---|---|---|---|---|
| | | | Average particle diameter (µm) | | | Amount of fine | SPAN | Pore capacity (% by mass) | | Specific | |
| | Type | Amount used (mmol) | Primary particle (D1) | Secondary particle (D2) | D1/D2 | powder[1] (% by mass) | Secondary particle (D2) | 1 µm or less | 0.1- 0.5 µm | surface area (m$^2$/g) | Bulk density (g/ml) |
| Example 1 to Example 5 | Bis(2-ethylhexyl)maleate | 30 | 0.6 | 57.8 | 0.01 | 0.0 | 0.8 | 0.7 | 0.5 | 14 | 0.32 |
| Example 6 | Diethyl maleate | 30 | 0.7 | 56.8 | 0.01 | 1.5 | 0.8 | 0.8 | 0.6 | 15 | 0.31 |
| Example 7 | Dimethyl diisobutylmalonate | 30 | 0.5 | 56.5 | 0.01 | 1.6 | 1.0 | 0.7 | 0.5 | 15 | 0.32 |
| Example 8 | Bis(2-ethylhexyl)maleate | 7 | 0.7 | 56.8 | 0.01 | 1.8 | 0.8 | 0.8 | 0.6 | 19 | 0.31 |
| Example 9 | Bis(2-ethylhexyl)maleate | 14 | 0.6 | 57.6 | 0.01 | 0.8 | 0.9 | 0.8 | 0.6 | 16 | 0.31 |
| Example 10 | Bis(2-ethylhexyl)maleate | 60 | 0.6 | 57.8 | 0.01 | 0.0 | 0.8 | 0.7 | 0.4 | 12 | 0.33 |
| Example 11 | Bis(2-ethylhexyl)maleate | 30 | 0.6 | 19.3 | 0.03 | 1.6 | 0.8 | 0.9 | 0.6 | 22 | 0.24 |
| Comparative Example 1 | None | 0 | 0.7 | 52.9 | 0.01 | 4.1 | 1.1 | 0.7 | 0.5 | 25 | 0.30 |
| Comparative Example 2 | 9,9-Bis(methoxymethyl)fluorene | 14 | 0.7 | 57.6 | 0.01 | 3.4 | 1.2 | 0.7 | 0.5 | 15 | 0.33 |

[1]Amount of fine powder means the amount of particles of 5 µm or less.

TABLE 2

|  | Internal electron-donating compound in solid catalyst component | Solid catalyst component properties | | Catalyst property Polymerization activity (g-pp/g-cat) | Polymer properties | | | |
|---|---|---|---|---|---|---|---|---|
|  |  | Average particle diameter D50 (μm) | Amount of fine powder having particle diameter of 5 μm (% by mass) |  | Bulk density (BD) (g/ml) | Amount of fine powder having particle diameter of 75 μm or less (% by mass) | Average particle diameter D50 (μm) | SPAN |
| Example 1 | Dimethyl diisobutylmalonate | 47.1 | 0.0 | 41,300 | 0.43 | 0.1 | 1,690 | 0.5 |
| Example 2 | Diethyl diisobutylmalonate | 46.3 | 0.2 | 47,700 | 0.4 | 0.1 | 1,730 | 0.6 |
| Example 3 | 2-Isopropyl 2-isopentyl-1,3-dimethoxypropane | 50.6 | 0.4 | 47,500 | 0.40 | 0.4 | 1,660 | 0.6 |
| Example 4 | Dibutyl phthalate | 48.5 | 0.6 | 55,000 | 0.42 | 0.3 | 1,720 | 0.6 |
| Example 5 | Dimethyl diisobutylmalonate + diethyl maleate | 49.2 | 0.0 | 31,500 | 0.44 | 0.1 | 1,490 | 0.4 |
| Example 6 | Dimethyl diisobutylmalonate | 45.6 | 0.5 | 39,900 | 0.43 | 0.3 | 1,590 | 0.5 |
| Example 7 | Dimethyl diisobutylmalonate | 46.1 | 0.5 | 24,000 | 0.44 | 0.5 | 1,280 | 0.5 |
| Example 8 | Dimethyl diisobutylmalonate | 45.6 | 0.8 | 36,100 | 0.44 | 0.3 | 1,490 | 0.5 |
| Example 9 | Dimethyl diisobutylmalonate | 47.4 | 0.0 | 35,400 | 0.44 | 0.1 | 1,500 | 0.5 |
| Example 10 | Dimethyl diisobutylmalonate | 48.9 | 0.0 | 33,000 | 0.45 | 0.1 | 1,520 | 0.4 |
| Example 11 | Dimethyl diisobutylmalonate | 19.2 | 0.1 | 41,800 | 0.41 | 0.2 | 580 | 0.8 |
| Comparative Example 1 | Dimethyl diisobutylmalonate | 57.1 | 3.5 | 38,100 | 0.40 | 1.5 | 1,640 | 0.6 |
| Comparative Example 2 | Dimethyl diisobutylmalonate | 47.2 | 3.5 | 39,300 | 0.41 | 1.2 | 1,690 | 0.6 |

From Table 1 and Table 2, it can be seen that, in Example 1 to Example 11, each of which includes use of an alkoxymagnesium obtained by reacting metal magnesium with the alcohol and then contacting the reactant with a carboxylic acid ester, composed of secondary particles each of which is an aggregate of primary particles, and having specific properties, each of the alkoxymagnesiums, when used as a constituent of a solid catalyst component for olefin polymerization to polymerize an olefin, may reduce the formation rate of a fine powder and form a polymer having an excellent particle size distribution under high polymerization activity.

Meanwhile, from Table 1 and Table 2, it can be seen that, in Comparative Example 1 and Comparative Example 2, in which the reactant is not contacted with a carboxylic acid ester after reaction of metal magnesium with the alcohol (Comparative Example 1) or the reactant is contacted with 9,9-bis(methoxymethyl)fluorene instead of a carboxylic acid ester (Comparative Example 2), each of the resulting alkoxymagnesiums having no specific properties is used, and thus, when such a alkoxymagnesium is used as a constituent of a solid catalyst component for olefin polymerization to polymerize an olefin, a large amount of a fine powder of especially 75 μm or less is formed.

INDUSTRIAL APPLICABILITY

According to the present invention, it is possible to provide a novel alkoxymagnesium which, when used as a constituent of a solid catalyst component for olefin polymerization to polymerize an olefin, may reduce the formation rate of a fine powder and form a polymer having an excellent particle size distribution under high polymerization activity as well as to provide a method for producing the alkoxymagnesium, a solid catalyst component for olefin polymerization, an olefin polymerization catalyst, and a method for producing an olefin polymer.

The invention claimed is:

1. An alkoxymagnesium comprising secondary particles each of which is an aggregate of primary particles having an average particle diameter of less than 1 μm, wherein
   a ratio of an average particle diameter of the primary particles/an average particle diameter of the secondary particles is 0.1 or less, a total pore volume is 0.5 to 1 cm³/g, a specific surface area is less than 50 m²/g, and a particle size distribution index (SPAN) is 1 or less.

2. The alkoxymagnesium according to claim 1, wherein a content of a fine powder having a particle diameter of 5 μm or less is 3% by mass or less based on a total particle mass, the total pore volume is 0.5 to 1 cm³/g, and 50% or more of pores having a pore diameter of 1 μm or less has a pore diameter of 0.5 μm or less.

3. The alkoxymagnesium according to claim 2, wherein the average particle diameter of the secondary particles is less than 60 μm.

4. The alkoxymagnesium according to claim 1, wherein the average particle diameter of the secondary particles is less than 60 μm.

5. A solid catalyst component for olefin polymerization obtained by contacting (a) the alkoxymagnesium according to claim 1, (b) a titanium halogen compound, and (c) an electron-donating compound with one another.

6. An olefin polymerization catalyst comprising (A) the solid catalyst component for olefin polymerization according to claim 5, (B) an organoaluminum compound represented by the following general formula (IV);

$$R^{15}{}_pAlQ_{3-p} \qquad (IV)$$

wherein $R^{15}$ represents an alkyl group having 1 to 4 carbon atoms, Q represents a hydrogen atom or halogen atom, and p is a real number satisfying $0<p\leq 3$, and when a plurality of $R^{15}$ are present, each $R^{15}$ may be identical or different from one another and when a plurality of Q are present, each Q may be identical or different from one another, and (C) an external electron-donating compound.

7. The olefin polymerization catalyst according to claim 6, wherein (C) the external electron-donating compound is one or more selected from organosilicon compounds represented by the following general formula (V);

$R^{16}_q Si(OR^{17})_{4-q}$ (V)

wherein $R^{16}$ represents an alkyl group having 1 to 12 carbon atoms, a vinyl group, an alkenyl group having 3 to 12 carbon atoms, a cycloalkyl group having 3 to 12 carbon atoms, a cycloalkenyl group having 3 to 12 carbon atoms, an aromatic hydrocarbon group having 6 to 15 carbon atoms, or an aromatic hydrocarbon group having 6 to 15 carbon atoms and having a substituent, and when a plurality of $R^{16}$ are present, the plurality of $R^{16}$ may be identical or different from one another, $R^{17}$ represents an alkyl group having 1 to 4 carbon atoms, a vinyl group, an alkenyl group having 3 to 12 carbon atoms, a cycloalkyl group having 3 to 6 carbon atoms, an aromatic hydrocarbon group having 6 to 12 carbon atoms, or an aromatic hydrocarbon group having 7 to 12 carbon atoms and having a substituent, and when a plurality of $R^{17}$ are present, the plurality of $R^{17}$ may be identical or different from one another, and q is an integer of $0 \leq q \leq 3$, or aminosilane compounds represented by the general formula (VI);

$(R^{18}R^{19}N)_s SiR^{20}_{4-s}$ (VI)

wherein $R^{18}$ and $R^{19}$ each represent a hydrogen atom, an alkyl group having 1 to 20 carbon atoms, a vinyl group, an alkenyl group having 3 to 20 carbon atoms, cycloalkyl group having 3 to 20 carbon atoms, a cycloalkenyl group having 3 to 20 carbon atoms, or an aryl group having 6 to 20 carbon atoms, $R^{18}$ and $R^{19}$ may be identical or different from each other or may bond with each other to form a ring, and when a plurality of $R^{18}R^{19}N$ groups are present, the plurality of $R^{18}R^{19}N$ groups may be identical or different from one another, $R^{20}$ represents an alkyl group having 1 to 20 carbon atoms, a vinyl group, an alkenyl group having 3 to 12 carbon atoms, an alkoxy group having 1 to 20 carbon atoms, a vinyloxy group having 3 to 20 carbon atoms, an alkenyloxy group having 3 to 20 carbon atoms, a cycloalkyl group having 3 to 20 carbon atoms, a cycloalkyloxy group having 3 to 20 carbon atoms, an aryl group having 6 to 20 carbon atoms, or an aryloxy group having 6 to 20 carbon atoms, and when a plurality of $R^{20}$ are present, the plurality of $R^{20}$ may be identical or different from one another, and s is an integer of 1 to 3.

8. A method for producing an olefin polymer comprising polymerizing an olefin in the presence of the olefin polymerization catalyst according to claim 6.

9. A method for producing an olefin polymer comprising polymerizing an olefin in the presence of the olefin polymerization catalyst according to claim 7.

10. A method for producing an alkoxymagnesium, comprising sequentially carrying out a solid formation step of reacting metal magnesium with an alcohol in the presence of a catalyst to form a solid, and a contact step of contacting the solid with one or more carboxylic acid esters in an organic solvent to form a suspension, wherein the one or more carboxylic acid ester is selected from diethyl succinate, dibutyl succinate, bis(2-ethylhexyl) succinate, diethyl maleate, dibutyl maleate, bis(2-ethylhexyl) maleate, diethyl malonate, dibutyl malonate, or bis(2-ethylhexyl) malonate.

11. The method for producing an alkoxymagnesium according to claim 10, wherein the alcohol is one or more selected from methanol, ethanol, n-propanol, isopropanol, n-butanol, isobutanol, or 2-ethylhexyl alcohol.

12. The method for producing an alkoxymagnesium according to claim 11, wherein the organic solvent is one or more selected from aliphatic hydrocarbon compounds or aromatic hydrocarbon compounds.

13. The method for producing an alkoxymagnesium according to claim 10, wherein the organic solvent is one or more selected from aliphatic hydrocarbon compounds or aromatic hydrocarbon compounds.

14. The method for producing an alkoxymagnesium according to claim 10, wherein the alkoxymagnesium is diethoxymagnesium.

15. The method for producing an alkoxymagnesium according to claim 10, wherein, by carrying out the contact step, a portion of the solid is reacted with the carboxylic acid ester to form a reactant, a portion of the solid is dissolved in a mixture of the carboxylic acid ester and the organic solvent, or a portion of the solid is liberated in a mixture of the carboxylic acid ester and the organic solvent.

* * * * *